United States Patent
Guillemont et al.

(10) Patent No.: US 7,442,705 B2
(45) Date of Patent: Oct. 28, 2008

(54) HIV REPLICATION INHIBITING PYRIMIDINES AND TRIAZINES

(75) Inventors: Jerôme Emile Georges Guillemont, Andé (FR); Elisabeth Thérese Jeanne Pasquier, Val-de-Reuil (FR); Jan Heeres, Vosselaar (BE); Kurt Hertogs, Antwerpen (BE); Eva Bettens, Zoersel (BE); Paulus Joannes Lewi, Turnhout (BE); Marc René De Jonge, CA Tilburg (NL); Lucien Maria Henricus Koymans, Retie (BE); Frederik Frans Desiré Daeyaert, Beerse (BE); Hendrik Maarten Vinkers, Antwerpen (BE); Paul Adriaan Jan Janssen, deceased, late of Brasschaat (BE); by Frank Xavier Jozef Herwig, legal representative, Brasschaat (BE)

(73) Assignee: Tibotec Pharmaceuticals Ltd (IE)

( * ) Notice: Subject to any disclaimer, the term of this patent is extended or adjusted under 35 U.S.C. 154(b) by 263 days.

(21) Appl. No.: 10/545,358

(22) PCT Filed: Feb. 20, 2004

(86) PCT No.: PCT/EP2004/050177

§ 371 (c)(1),
(2), (4) Date: Aug. 12, 2005

(87) PCT Pub. No.: WO2004/074262

PCT Pub. Date: Sep. 2, 2004

(65) Prior Publication Data

US 2006/0194804 A1 Aug. 31, 2006

Related U.S. Application Data

(60) Provisional application No. 60/475,012, filed on Jun. 2, 2003.

(30) Foreign Application Priority Data

Feb. 20, 2003 (EP) .................................. 03100411

(51) Int. Cl.
*C07D 239/47* (2006.01)
*C07D 239/48* (2006.01)
*C07D 407/12* (2006.01)
*A61K 31/505* (2006.01)
*A61P 31/18* (2006.01)

(52) U.S. Cl. ...................... 514/272; 514/275; 544/321; 544/323; 544/324

(58) Field of Classification Search ................. 544/238, 544/295, 320, 321, 324, 323; 514/272, 275
See application file for complete search history.

(56) References Cited

U.S. PATENT DOCUMENTS

| 3,459,731 A | 8/1969 | Gramera et al. |
| 5,691,364 A | 11/1997 | Buckman et al. |
| 2006/0142571 A1 | 6/2006 | Guillemont et al. |

FOREIGN PATENT DOCUMENTS

| EP | 0 834 507 A1 | 4/1998 |
| WO | WO 97/18839 | 5/1997 |
| WO | WO 98/41512 | 9/1998 |
| WO | WO 99/50250 | 10/1999 |
| WO | WO 99/50256 | 10/1999 |
| WO | WO 00/27825 | 5/2000 |
| WO | WO 00/62778 | 10/2000 |
| WO | WO 00/78731 | 12/2000 |
| WO | WO 01/85700 | 11/2001 |
| WO | WO 02/36578 | 5/2002 |

OTHER PUBLICATIONS

Anderson et al., Annu. Rev. Microbiol., 58:183-205, 2004.*
Vasu Nair Rev, Med. Viro. 12;179-193, 2002.*
Turner et al., Current Pharmaceutical Design. 2, 209-224, 1996.*
Sugar et al., Diagn. Microbiol. Infect. Dis. 21: 129-133, 1995.*
Snyder et al., J. Med. Liban 48(4): 208-214, 2000.*
Daifuku Biodrugs17(3); 169-177, 2003.*
International Search Report dated Jun. 14, 2004 for related International Application No. PCT/EP2003/050177.
Larock, R., John Wiley & Sons, Inc, 1999, p. 1983-1985.
Nogardi, M., Drugs of the Future, vol. 9, No. 8, 1984, p. 577-578.

* cited by examiner

*Primary Examiner*—Venkataraman Balasubram

(57) ABSTRACT

This invention concerns HIV replication inhibitors of formula (I), The N-oxides, the pharmaceutically acceptable addition salts, the quaternary amines and the stereochemically isomeric forms thereof, their use as a medicine, their processes for preparation and pharmaceutical compositions comprising them.

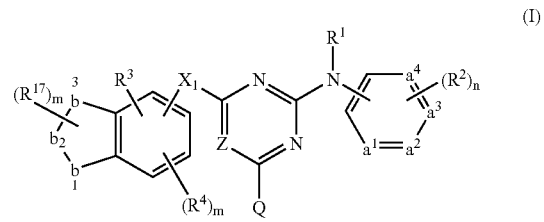

11 Claims, No Drawings

HIV REPLICATION INHIBITING PYRIMIDINES AND TRIAZINES

This application is a 371 of PCT/EP04/50177 Feb. 20, 2004 which claims benefit of U.S. Provisional Application No. 60/475,012, filed Jun. 2, 2003.

The present invention is concerned with pyrimidine and triazine derivatives having HIV (Human Immunodeficiency Virus) replication inhibiting properties. The invention further relates to methods for their preparation and pharmaceutical compositions comprising them. The invention also relates to the use of said derivatives for the manufacture of a medicament for the prevention or the treatment of HIV infection.

The present invention is aimed at providing particular novel series of pyrimidine derivatives having HIV replication properties. WO 99/50250, WO 00/27825 and WO 01/85700 disclose certain substituted aminopyrimidines and WO 99/50256 and EP-834 507 disclose aminotriazines having HIV replication inhibiting properties.

The compounds of the invention differ from the prior art compounds in structure, pharmacological activity and/or pharmacological potency. It has been found that the compounds of the invention not only act favorably in terms of their capability to inhibit the replication of Human Immunodeficiency Virus (HIV), but also by their improved ability to inhibit the replication of mutant strains, in particular strains which have become resistant to commercially available drugs (so-called drug or multidrug resistant HIV strains).

Thus in one aspect, the present invention concerns a compound of formula

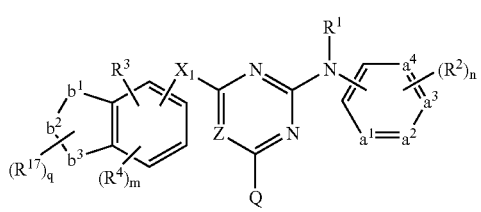

(I)

a N-oxide, a pharmaceutically acceptable addition salt, a quaternary amine or a stereochemically isomeric form thereof, wherein
-$a^1$=$a^2$-$a^3$=$a^4$- represents a bivalent radical of formula —CH=CH—CH=CH—      (a-1);

—N=CH—CH=CH—      (a-2);

—N=CH—N=CH—      (a-3);

—N=CH—CH=N—      (a-4);

—N=N—CH=CH—      (a-5);

-$b^1$-$b^2$-$b^3$- represents a bivalent radical of formula

—O—CH$_2$—CH$_2$—      (b-1);

—O—CH=CH—      (b-2);

—S—CH$_2$—CH$_2$—      (b-3);

—S—CH=CH—      (b-4);

—CH$_2$—CH=CH—      (b-5);

n is 0, 1, 2, 3 or 4; and in case -$a^1$=$a^2$-$a^3$=$a^4$- is (a-1), then n may also be 5;
m is 0, 1, 2, 3;
q is 0, 1 or 2;
p is 1 or 2;
$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
each $R^2$ independently is hydroxy, halo, $C_{1-6}$alkyl optionally substituted with cyano or with —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, $NR^{13}R^{14}$, polyhalomethyl, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

(c)

wherein each $A_1$ independently is N, CH or $CR^6$; and
$A_2$ is NH, O, S or $NR^6$;
$X_1$ is —$NR^5$—, —NH—NH—, —N=N—, —O—, —C(=O)—, $C_{1-4}$alkanediyl, —CHOH—, —S—, —S(=O)$_p$—, —$NR^{13}$—C(=O)—, —C(=O)—$NR^{13}$—, —$X_2$—$C_{1-4}$alkanediyl- or —$C_{1-4}$alkanediyl-$X_2$—;
$X_2$ is —$NR^5$—, —NH—NH—, —N=N—, —O—, —C(=O)—, —CHOH—, —S—, —S(=O)$_p$—;
$R^3$ is hydrogen, halo, $C_{1-6}$alkyl, $NR^{13}R^{14}$, —C(=O)—$NR^{13}R^{14}$, —C(=O)—$R^{15}$, —CH=N—NH—C(=O)—$R^{16}$, —C(=N—O—$R^8$)—$C_{1-4}$alkyl, $R^7$ or —$X_3$—$R^7$; or $C_{1-6}$alkyl substituted with one or more substituents each independently selected from halo, hydroxy, cyano, $NR^9R^{10}$, —C(=O)—$NR^9R^{10}$, —C(=O)—$C_{1-6}$alkyl or $R^7$, and in addition to said list of substituents, two geminal hydrogen atoms of said $C_{1-6}$alkyl may also be replaced by a $C_{2-5}$alkanediyl thus forming a spiro ring; $C_{1-6}$alkyloxy$C_{1-6}$alkyl optionally substituted with one or more substituents each independently selected from hydroxy, cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, hydroxy, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, hydroxy, cyano, $NR^9R^{10}$, —C(=O)—$NR^9R^{10}$, —C(=O)—$C_{1-6}$alkyl or $R^7$;
$X_3$ is —$NR^5$—, —NH—NH—, —N=N—, —O—, —C(=O)—, —S—, —S(=O)$_p$—, —$X_2$—$C_{1-4}$alkanediyl-, —$C_{1-4}$alkanediyl-$X_{2a}$—, —$C_{1-4}$alkanediyl-$X_{2b}$—$C_{1-4}$alkanediyl, —C(=N—OR$^8$)—$C_{1-4}$alkanediyl-;
with $X_{2a}$ being —NH—NH—, —N=N—, —O—, —C(=O)—, —S—, —S(=O)$_p$—; and
with $X_{2b}$ being —NH—NH—, —N=N—, —C(=O)—, —S—, —S(=O)$_p$—;
$R^4$ is halo, hydroxy, $C_{1-6}$alkyl, $C_{2-6}$alkenyl, $C_{2-6}$alkynyl, $C_{3-7}$cycloalkyl, $C_{1-6}$alkyloxy, cyano, nitro, polyhalo$C_{1-6}$ alkyl, polyhalo$C_{1-6}$alkyloxy, —C(=O)—$NR^{13}R^{14}$, $C_{1-6}$alkyloxycarbonyl, $C_{1-6}$alkylcarbonyl, formyl, —$NR^{13}R^{14}$ or $R^7$;

$R^5$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl or $C_{1-6}$alkylcarbonyloxy; $C_{1-6}$alkyloxy$C_{1-6}$alkylcarbonyl substituted with $C_{1-6}$alkyloxycarbonyl;

$R^6$ is $C_{1-4}$alkyl, $NR^{13}R^{14}$ or polyhalo$C_{1-4}$alkyl;

$R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$ alkyl;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, —C(=O)—$NR^{13}R^{14}$, —CH(=N—O—$R^8$);

$R^8$ is hydrogen, $C_{1-4}$alkyl, aryl or aryl$C_{1-4}$alkyl;

$R^9$ and $R^{10}$ each independently are hydrogen; hydroxy; $C_{1-6}$alkyl; $C_{1-6}$alkyloxy; $C_{1-6}$alkylcarbonyl; $C_{1-6}$alkyloxycarbonyl; $NR^{13}R^{14}$; —C(=O)—$NR^{13}R^{14}$; —CH(=$NR^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, imino, $NR^{13}R^{14}$, polyhalomethyl, polyhalomethyloxy, polyhalomethylthio, —S(=O)$_p R^6$, —NH—S(=O)$_p R^6$, —C(=O)$R^6$, —NHC(=O)H, —C(=O)NHNH$_2$, —NHC(=O)$R^6$, —C(=NH)$R^6$, $R^7$; or $R^9$ and $R^{10}$ may be taken together to form a bivalent or trivalent radical of formula —CH$_2$—CH$_2$—CH$_2$—CH$_2$— (d-1)

—CH$_2$—CH$_2$—CH$_2$—CH$_2$—CH$_2$— (d-2)

—CH$_2$—CH$_2$—O—CH$_2$—CH$_2$— (d-3)

—CH$_2$—CH$_2$—S—CH$_2$—CH$_2$— (d-4)

—CH$_2$—CH$_2$—$NR^{12}$—CH$_2$—CH$_2$— (d-5)

—CH$_2$—CH=CH—CH$_2$— (d-6)

=CH—CH=CH—CH=CH— (d-7)

$R^{11}$ is cyano; $C_{1-4}$alkylcarbonyl; $C_{1-4}$alkyloxycarbonyl; —C(=O)—$NR^{13}R^{14}$; or $C_{1-4}$alkyl optionally substituted with $C_{1-4}$alkyloxy, cyano, $NR^{13}R^{14}$ or —C(=O)—$NR^{13}R^{14}$;

$R^{12}$ is hydrogen or $C_{1-4}$alkyl;

$R^{13}$ and $R^{14}$ each independently are hydrogen, Het, $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ is $C_{1-6}$alkyl optionally substituted with cyano or —C(=O)—$NR^{13}R^{14}$;

$R^{16}$ is $R^7$ or $C_{1-6}$alkyl optionally substituted with cyano or —C(=O)—$NR^{13}R^{14}$;

$R^{17}$, if present, each independently is cyano, halo, hydroxy, —C(=O)—$NR^{13}R^{14}$, $C_{1-6}$alkyl optionally substituted with one or more substituents independently selected from cyano, —C(=O)—$NR^{13}R^{14}$ or halo; $C_{2-6}$alkenyl optionally substituted with one or more substituents independently selected from cyano, —C(=O)—$NR^{13}R^{14}$ or halo; $C_{2-6}$alkynyl optionally substituted with one or more substituents independently selected from cyano, —C(=O)—$NR^{13}R^{14}$ or halo; and, where possible, $R^{17}$ may also be attached to the -b$^1$-b$^2$-b$^3$- moiety by a double bond whereby $R^{17}$ is then =O, =S, =NH, =N—$R^{15}$, =N—$R^7$, =N—O—$R^{15}$, =N—O—$R^7$, =CH$_2$, =CH—C(=O)—$NR^{13}R^{14}$, =CH—$R^7$, or =CH—$R^{15}$; wherein =CH$_2$ may optionally be substituted with cyano, hydroxy, halo, nitro;

Q represents hydrogen, $C_{1-6}$alkyl, halo, polyhalo$C_{1-6}$alkyl, —C(=O)—$NR^{13}R^{14}$, or —$NR^9R^{10}$;

Z is C—Y or N, wherein,

Y represents hydrogen, hydroxy, halo, $C_{1-6}$alkyl, $C_{3-7}$cycloalkyl, $C_{1-6}$alkyloxy, $C_{1-6}$alkyloxycarbonyl, carbonyl, cyano, nitro, $NR^{13}R^{14}$, polyhalomethyl, polyhalomethyloxy, polyhalomethylthio, —S(=O)$_p R^8$, —NH—S(=O)$R^8$, —NH—SO$_2$—$R^8$, —NH—SO$_2$—($C_{1-4}$alkanediyl)-CO—N($R^8$)$_2$, —C(=O)$R^8$, —NHC(=O)H, —C(=O)NHNH$_2$, —NHC(=O)$R^8$, —C(=O)—NH—$R^8$, —C(=NH)$R^8$, aryl or $C_{2-6}$alkenyl optionally substituted with one or more halo atoms; $C_{2-6}$alkynyl optionally substituted with one ore more halo atoms; $C_{1-6}$alkyl substituted with cyano or with —C(=O)$R^8$;

aryl is phenyl or phenyl substituted with one, two, three, four or five substituents each independently selected from halo, hydroxy, mercapto, $C_{1-6}$alkyl, hydroxy$C_{1-6}$alkyl, $C_{1-6}$alkyl$NR^{13}R^{14}$, $C_{1-6}$alkylcarbonyl, $C_{3-7}$cycloalkyl, $C_{1-6}$alkyloxy, $C_{1-6}$alkyloxy-carbonyl, $C_{1-6}$alkylthio, cyano, nitro, polyhalo$C_{1-6}$alkyl, polyhalo$C_{1-6}$alkyloxy, —C(=O)—$NR^{13}R^{14}$, $R^7$ or —$X_3$—$R^7$.

Het is a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, —C(=O)—$NR^{13}R^{14}$, —CH(=N—O—$R^8$).

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methyl-butyl and the like; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like.

In a number of instances the radicals $C_{1-6}$alkynyl, $C_{2-6}$alkenyl, or $C_{2-6}$alkynyl may be substituted with one or more substituents. In that instance there can be 1, 2, 3, 4, 5, 6 and more substituents, the number in some cases being limited by the number of carnbon atoms and the degree of unsaturation of the hydrocarbon radical. Preferably, the radicals $C_{1-6}$alkynyl, $C_{2-6}$alkenyl, or $C_{2-6}$alkynyl are substituted with up to 3 substituents.

A monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like. Preferred are cyclopropyl, cyclobutyl, cyclopentyl, cyclohexyl, cycloheptyl; more preferred are cyclopentyl, cyclohexyl, cycloheptyl.

Particular examples of monocyclic, bicyclic or tricyclic partially saturated carbocycles are cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronapllthalenyl, 1,2,3,4-tetrahydronaphthalenyl, 1,2,3,4,4a,9,9a,10-octahydro-anthracenyl and the like. Preferred are cyclopentenyl, cyclohexenyl, cycloheptenyl.

Particular examples of monocyclic, bicyclic or tricyclic aromatic carbocycles are phenyl, naphthalenyl, anthracenyl. Preferred is phenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl and the like. Preferred are tetrahydrofuranyl, pyrrolidinyl, dioxolanyl, imidazolidinyl, thiazolidinyl, dihydrooxazolyl, triazolidinyl, piperidinyl, dioxanyl, morpholinyl, thiomorpholinyl, piperazinyl. Particularly preferred are tetrahydrofuranyl, pyrrolidinyl, dioxolanyl, piperidinyl, dioxanyl, morpholinyl, thiomorpholinyl, piperazinyl Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like. Preferred are pyrrolinyl, imidazolinyl, 2,3-dihydrobenzofuranyl, 1,3-benzodioxolyl, indolinyl.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

Preferred aromatic heterocycles are monocyclic or bicyclic aromatic heterocycles. Interesting monocyclic, bicyclic or tricyclic aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, carbazolyl, acridinyl, phenothiazinyl, phenoxazinyl and the like.

Particularly interesting aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-6}$alkyl or $C_{1-6}$alkyl, for example, the groups defined in halomethyl, 1,1-difluoro-ethyl and the like. In case more than one halogen atoms are attached to an alkyl group within the definition of polyhalomethyl, polyhalo$C_{1-4}$alkyl or polyhalo$C_{1-6}$alkyl, they may be the same or different.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (eg. $R^7$, heteroatom, $X_2$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, maionic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms (solvates) which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

For some of the compounds of formula (I), their prodrugs, N-oxides, salts, solvates, quaternary amines or metal complexes and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

Whenever used hereinbefore or hereinafter that substituents can be selected each independently out of a list of numerous definitions, such as for example for $R^9$ and $R^{10}$, all possible combinations are intended which are chemically possible and which lead to chemically stable molecules.

A particular subgroup of the compounds of formula (I) are those wherein Z is N. Another subgroup are the compounds of formula (I) wherein Z is C—Y.

A particular subgroup of the compounds of formula (I) are those wherein -$b^1$-$b^2$-$b^3$- represents a bivalent radical of formula —O—CH$_2$—CH$_2$— (b-1)

—O—CH=CH— (b-2)

—S—CH$_2$—CH$_2$— (b-3)

—S—CH=CH— (b-4).

Of this subgroup of compounds, those wherein -$b^1$-$b^2$-$b^3$- is a radical (b-1) or (b-2) are of specific interest.

Another particular subgroup of the compounds of formula (I) are those wherein -$b^1$-$b^2$-$b^3$- represents a bivalent radical of formula —CH$_2$—CH=CH— (b-5)

Other subgroups are those wherein the above specified limitations for as well Z as -$b^1$-$b^2$-$b^3$- apply.

Subgroups of the compounds of formula (I) that are of interest are those wherein one or more of the following limitations (a)-(v) apply.

(a) -$a^1$=$a^2$-$a^3$=$a^4$- represents a bivalent radical of formula

—CH=CH—CH=CH— (a-1);

(b) n is 0, 1, 2, 3;
(c) m is 0, 1 or 2;
(d) $R^1$ is hydrogen; formyl; $C_{1-6}$alkylcarbonyl; $C_{1-6}$alkyl; $C_{1-6}$alkyloxycarbonyl; $C_{1-6}$alkylcarbonyl, $C_{1-6}$alkyloxycarbonyl;
(e) each $R^2$ independently is hydroxy, halo, $C_{1-6}$alkyl optionally substituted with cyano or with —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono($C_{1-6}$alkyl)amino, di($C_{1-6}$alkyl)amino, polyhalomethyl, polyhalomethylthio, —S(=O)$_p$$R^6$, —NH—S(=O)$_p$ $R^6$, —C(=O)$R^6$, —NHC(=O)H, —C(=O)NHNH$_2$, —NHC(=O)$R^6$, —C(=NH)$R^6$ or a radical of formula

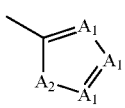

(c)

wherein each $A_1$ independently is N, CH or CR$^6$; and $A_2$ is NH, O, S or NR$^6$;

(f) $X_1$ is —NR$^5$—, —NH—NH—, —N=N—, —O—, —C(=O)—, $C_{1-4}$alkanediyl, —CHOH—, —S—, —S(=O)$_p$—, —NR$^{13}$—C(=O)—, —C(=O)—NR$^{13}$—, —$X_2$—$C_{1-4}$alkanediyl- or —$C_{1-4}$alkanediyl-$X_2$—;

(g) $X_2$ is —NR$^5$—, —O—;

(h) $R^3$ is hydrogen, halo, $C_{1-6}$alkyl, NR$^{13}$R$^{14}$, —C(=O)—NR$^{13}$R$^{14}$, —C(=O)—R$^{15}$, —$X_3$—R$^7$; $C_{1-6}$alkyl substituted with one or more substituents each independently selected from cyano, $R^7$ or —C(=O)—NR$^9$R$^{10}$; $C_{2-6}$alkenyl substituted with one or more substituents each independently selected from halo, cyano or —C(=O)—NR$^9$R$^{10}$ or $R^7$; or $C_{2-6}$alkynyl substituted with one or more substituents each independently selected from halo, cyano, —C(=O)—NR$^9$R$^{10}$ or $R^7$;

(i) $X_3$ is —NR$^5$—, —NH—NH—, —N=N—, —O— or —S—

(j) $R^4$ is halo, hydroxy, $C_{1-6}$alkyl, $C_{2-6}$alkenyl, $C_{2-6}$alkynyl, $C_{1-6}$alkyloxy, cyano, nitro, polyhalo$C_{1-6}$alkyl, polyhaloC$_{1-6}$ alkyloxy, —C(=O)—NR$^{13}$R$^{14}$, $C_{1-6}$alkyloxycarbonyl, $C_{1-6}$alkylcarbonyl, formyl, —NR$^{13}$R$^{14}$ or $R^7$;

(k) $R^5$ is hydrogen; formyl; $C_{1-6}$alkylcarbonyl; $C_{1-6}$alkyl or $C_{1-6}$alkyloxycarbonyl;

(l) $R^6$ is $C_{1-4}$alkyl, NR$^{13}$R$^{14}$ or polyhalo$C_{1-4}$alkyl;

(m) $R^7$ is a monocyclic or bicyclic, partially saturated or aromatic carbocycle or a monocyclic or bicyclic, partially saturated or aromatic heterocycle, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl;

(n) $R^8$ is hydrogen, $C_{1-4}$alkyl or aryl$C_{1-4}$alkyl;
(o) $R^9$ and $R^{10}$ each independently are hydrogen; $C_{1-6}$alkyl; $C_{1-6}$alkyloxy; $C_{1-6}$alkylcarbonyl or $C_{1-6}$alkyloxycarbonyl;

(p) $R^{13}$ and $R^{14}$ each independently are hydrogen or $C_{1-6}$alkyl;

(q) $R^{15}$ is $C_{1-6}$alkyl optionally substituted with cyano or —C(=O)—$NR^{13}R^{14}$;

(r) $R^{17}$ is cyano, halo, hydroxy, —C(=O)—$NR^{13}R^{14}$, $C_{1-6}$alkyl optionally substituted with cyano, —C(=O)—$NR^{13}R^{14}$ or halo; $C_{2-6}$alkenyl optionally substituted with cyano or —C(=O)—$NR^{13}R^{14}$; $C_{2-6}$alkynyl optionally substituted with cyano or —C(=O)—$NR^{13}R^{14}$; and, where possible, $R^{17}$ may also be attached to the -$b^1$-$b^2$-$b^3$- moiety by a double bond whereby $R^{17}$ is then =O, =S, =NH, =N—$R^{15}$, =N—$R^7$, =N—O—$R^{15}$, =N—O—$R^7$, =$CH_2$, =CH—C(=O)—$NR^{13}R^{14}$, =CH—$R^7$, or =CH—$R^{15}$; wherein =$CH_2$ may optionally be substituted with cyano, hydroxy, halo, nitro;

(s) Q represents hydrogen, $C_{1-6}$alkyl or —$NR^9R^{10}$;

(t) Y represents hydrogen, hydroxy, halo, $C_{1-6}$alkyl, $C_{1-6}$alkyloxy, cyano, nitro, $NR^{13}R^{14}$, polyhalomethyloxy, —NH—$SO_2$—$R^8$, —NH—$SO_2$—($C_{1-4}$alkanediyl)-CO—N($R^8$)$_2$; or Y is $C_{1-6}$alkyl substituted with cyano or with —C(=O) $R^8$, (u) aryl is phenyl or phenyl substituted with one, two or three substituents each independently selected from halo, hydroxy, mercapto, $C_{1-6}$alkyl, hydroxy$C_{1-6}$alkyl, $C_{1-6}$alkyl$NR^{13}R^{14}$, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, —C(=O)—$NR^{13}R^{14}$, $R^7$ or —$X_3$—$R^7$;

(v) Het is a monocyclic or bicyclic, partially saturated or aromatic heterocycle, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy.

A particularly interesting subgroup of compounds of formula (I) are those wherein all of the above limitations (a)-(v) apply.

Of further interest are subgroups of the compounds of formula (I) wherein one or more of the afore mentioned limitations (a)-(v) optionally apply and one or more of the following limitations (a')-(v') apply:

(a') -$a^1$=$a^2$-$a^3$=$a^4$- represents a bivalent radical of formula

—CH=CH—CH=CH—                (a-1);

(b') n is 1 or 2;

(c') m is 1 or 2;

(d') $R^1$ is hydrogen; $C_{1-6}$alkyl;

(e') each $R^2$ independently is hydroxy, halo, $C_{1-6}$alkyl optionally substituted with cyano or with —C(=O)$R^6$, $C_{2-6}$alkenyl optionally substituted with cyano, $C_{2-6}$alkynyl optionally substituted with cyano, $C_{1-6}$alkyloxycarbonyl, carboxyl, cyano, nitro, amino, mono($C_{1-6}$alkyl)amino, di($C_{1-6}$alkyl)amino, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

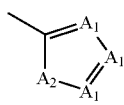
(c)

wherein each $A_1$ independently is N, CH or $CR^6$; and no more than two $A_1$ are N;

$A_2$ is NH, O, S or $NR^6$;

(f') $X_1$ is —$NR^5$—, —NH—NH—, —N=N—, —O—, —C(=O)—, $C_{1-4}$alkanediyl, —CHOH—, —$NR^{13}$—C(=O)—, —C(=O)—$NR^{13}$—, —$X_2$—$C_{1-4}$alkanediyl- or —$C_{1-4}$alkanediyl-$X_2$—;

(g') $X_2$ is —$NR^5$—, —O—;

(h') $R^3$ is hydrogen, halo, $C_{1-6}$alkyl, $NR^{13}R^{14}$, —C(=O)—$NR^{13}R^{14}$, —C(=O)—$NR^{15}$, —$X_3$—$R^7$; $C_{1-6}$alkyl substituted with one or two substituents each independently selected from cyano, $R^7$ or —C(=O)—$NR^9R^{10}$; $C_{2-6}$alkenyl substituted with one or more substituents each independently selected from halo, cyano or —C(=O)—$NR^9R^{10}$; or $C_{2-6}$alkynyl substituted with one or more substituents each independently selected from halo, cyano, —C(=O)—$NR^9R^{10}$;

(i') $X_3$ is —$NR^5$-or-O—;

(j') $R^4$ is halo, hydroxy, $C_{1-6}$alkyl, $C_{2-6}$alkenyl, $C_{2-6}$alkynyl, $C_{1-6}$alkyloxy, cyano, nitro, —C(=O)—$NR^{13}R^{14}$, $C_{1-6}$alkyloxycarbonyl, $C_{1-6}$alkylcarbonyl, formyl, —$NR^{13}R^{14}$;

(k') $R^5$ is hydrogen; $C_{1-4}$alkyl;

(l') $R^6$ is $C_{1-4}$alkyl;

(m') $R^7$ is any of the specific monocyclic or bicyclic, partially saturated or aromatic carbocycles or monocyclic or bicyclic, partially saturated or aromatic heterocycles specifically mentioned in this specification, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl;

(n') $R^8$ is hydrogen or $C_{1-4}$alkyl;

(o') $R^9$ and $R^{10}$ each independently are hydrogen or $C_{1-6}$alkyl;

(p') $R^{13}$ and $R^{14}$ each independently are hydrogen or $C_{1-6}$alkyl;

(q') $R^{15}$ is $C_{1-6}$alkyl optionally substituted with cyano or —C(=O)—$NR^{13}R^{14}$;

(r') $R^{17}$ is cyano, halo, hydroxy, —C(=O)—$NR^{13}R^{14}$, $C_{1-6}$alkyl optionally substituted with cyano, —C(=O)—$NR^{13}R^{14}$; $C_{2-6}$alkenyl optionally substituted with cyano or —C(=O)—$NR^{13}R^{14}$; $C_{2-6}$alkynyl optionally substituted with cyano or —C(=O)—$NR^{13}R^{14}$; and, where possible, $R^{17}$ may also be attached to the -$b^1$-$b^2$-$b^3$- moiety by a double bond whereby $R^{17}$ is then =O, =NH, =N—$R^{15}$, =N—$R^7$, =N—O—$R^{15}$, =N—O—$R^7$, =$CH_2$, =CH—C(=O)—$NR^{13}R^{14}$, =CH—$R^7$, or =CH—$R^{15}$; wherein =$CH_2$ may optionally be substituted with cyano;

(s') Q represents hydrogen or $C_{1-6}$alkyl or —$NR^9R^{10}$;

(t') Y represents hydrogen, hydroxy, halo, $C_{1-6}$alkyl, $C_{1-6}$alkyloxy, cyano, nitro, $NR^{13}R^{14}$, polyhalomethyloxy, —NH—$SO_2$—$R^8$, —NH—$SO_2$—($C_{1-4}$alkanediyl)-CO—N($R^8$)$_2$;

(u') aryl is phenyl or phenyl substituted with one, two or three substituents each independently selected from halo, hydroxy, $C_{1-6}$alkyl, hydroxy$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, —C(=O)—$NR^{13}R^{14}$;

(v') Het is a monocyclic or bicyclic, partially saturated or aromatic heterocycle, specifically mentioned in this specification, wherein each of said heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy.

A specific subgroup of the compounds of formula (I) are those wherein all of the limitations (a')-(v') of the previous paragraph apply.

Of particular interest are any subgroups of the compounds of formula (I) wherein one or more of the afore mentioned limitations (a)-(v) or of the limitations (a')-(v') optionally apply as well as one or more of the following limitations (a")-(v"):

(a") -a$^1$=a$^2$-a$^3$-a$^4$- represents a bivalent radical of formula

  (a-1);

(b") n is 1;
(c") m is 1;
(d") R$^1$ is hydrogen; methyl;
(e") R$^2$ is halo, $C_{1-6}$alkyl optionally substituted with cyano, $C_{2-6}$alkenyl optionally substituted with cyano, $C_{2-6}$alkynyl optionally substituted with cyano, $C_{1-6}$alkyloxycarbonyl, carboxyl, cyano, amino, mono($C_{1-6}$alkyl)amino, di($C_{1-6}$alkyl)amino;
(f") $X_1$ is —NR$^5$—, —O—, —NR$^{13}$—C(=O)—, —C(=O)—NR$^{13}$—;
(h") R$^3$ is hydrogen, halo, $C_{1-6}$alkyl, NR$^{13}$R$^{14}$, —C(=O)—NR$^{13}$R$^{14}$, —C(=O)—R$^{15}$; $C_{1-6}$alkyl substituted with cyano; $C_{2-6}$alkenyl substituted with cyano; or $C_{2-6}$alkynyl substituted with cyano;
(j") R$^4$ is halo, hydroxy, $C_{1-6}$alkyl, $C_{2-6}$alkenyl, $C_{2-6}$alkynyl, $C_{1-6}$alkyloxy, cyano, nitro —C(=O)—NR$^{13}$R$^{14}$, —NR$^{13}$R$^{14}$;
(k") R$^5$ is hydrogen; $C_{1-6}$alkyl;
(m") R$^7$ is any of the specific monocyclic or bicyclic, partially saturated or aromatic carbocycles or monocyclic or bicyclic, partially saturated or aromatic heterocycles specifically mentioned in this specification, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl;
(n") R$^8$ is hydrogen or $C_{1-4}$alkyl;
(o") R$^9$ and R$^{10}$ are hydrogen;
(p") R$^{13}$ and R$^{14}$ are hydrogen;
(q") R$^{15}$ is $C_{1-6}$alkyl optionally substituted with cyano;
(r") R$^{17}$ is cyano, —C(=O)—NR$^{13}$R$^{14}$, $C_{1-6}$alkyl optionally substituted with cyano, —C(=O)—NR$^{13}$R$^{14}$; $C_{2-6}$alkenyl optionally substituted with cyano or —C(=O)—NR$^{13}$R$^{14}$; $C_{2-6}$alkynyl optionally substituted with cyano or —C(=O)—NR$^{13}$R$^{14}$; and, where possible, R$^{17}$ may also be attached to the -b$^1$-b$^2$-b$^3$- moiety by a double bond whereby R$^{17}$ is then =O, =NH, =N—R$^{15}$, =N—R$^7$, =N—O—R$^{15}$, =N—O—R$^7$, =CH$_2$, =CH—C(=O)—NR$^{13}$R$^{14}$, =CH—R$^7$, or =CH—R$^{15}$; wherein =CH$_2$ may optionally be substituted with cyano;
(s") Q represents hydrogen or —NR$^9$R$^{10}$;
(t") Y represents hydrogen, hydroxy, halo, $C_{1-6}$alkyl, $C_{1-6}$alkyloxy, cyano, NR$^{13}$R$^{14}$, —NH—SO$_2$—R$^8$, —NH—SO$_2$—($C_{1-4}$alkanediyl)-CO—N(R$^8$)$_2$;
(u") aryl is phenyl or phenyl substituted with one, two or three substituents each independently selected from halo, hydroxy, $C_{1-6}$alkyl, $C_{1-6}$alkyloxy, $C_{1-6}$alkylthio, cyano, nitro;
(v") Het is a monocyclic or bicyclic, partially saturated or aromatic heterocycle, specifically mentioned in this specification, wherein each of said heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy.

A specific subgroup of the compounds of formula (I) are those wherein all of the limitations (a")-(v") of the previous paragraph apply.

For those compounds of formula (I) wherein -b1-b2-b3- is (b-5) the subgroups wherein one or more of the following conditions apply are of specific interest.

(a-1) -a$^1$=a$^2$-a$^3$=a$^4$- represents a bivalent radical of formula  (a-1).

(a-2) m is 0, 1 or 2, in particular 1 or 2, more in particular 2; and wherein the R$^4$ substituents are placed in the ortho position in respect of the $X_1$ moiety;

(a-3) $X_1$ is linked to one of the carbon atoms in meta position of the carbon atoms common to both rings of the bicyclic ring system to which $X_1$ is connected;

(a-4) where applicable n is 0 or n is 1 and the R$^2$ substituent is placed in position 4 (para position) in respect of the NR$^1$-linker;

(a-5) R$^2$ is hydroxy, halo, $C_{1-6}$alkyl optionally substituted with cyano or with —C(=O)R$^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(=O)$_p$R$^6$, —NH—S(=O)$_p$R$^6$, —NHC(=O)H, —C(=O)NHNH$_2$, —NHC(=O)R$^6$, —C(=NH)R$^6$ or a radical of formula

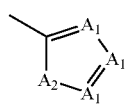 (c)

wherein each $A_1$ independently is N, CH or CR$^6$; and $A_2$ is NH, O, S or NR$^6$;

(a-6) R$^3$ is $C_{1-6}$alkyl optionally substituted with cyano.

For those compounds of formula (I) wherein -b$^1$-b$^2$-b$^3$- is (b-3) or (b-2) or (b-3) or (b-4) the following subgroups wherein one or wherever possible more of the following conditions apply, are interesting:

(c-1) m is 1, 2 or 3, in particular 2 or 3, more in particular 2, even more in particular m is 2 and said two R$^4$ substituents are placed in position 2 and 6 (ortho position) in respect of the $X_1$ moiety;

(c-2) $X_1$ is linked to one of the carbon atoms in meta position of the carbon atoms common to both rings of the bicyclic ring system to which $X_1$ is connected;

(c-3) where applicable n is 0; n is 1 and said R$^2$ substituent is placed in position 4 (para position) in respect of the NR$^1$-linker;

(c-4) R$^2$ is hydroxy, halo, $C_{1-6}$alkyl optionally substituted with cyano or with —C(=O)R$^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(=O)$_p$R$^6$, —NH—S(=O)$_p$R$^6$, —NHC(=O)H, —C(=O)NHNH$_2$, —NHC(=O)R$^6$, —C(=NH)R$^6$ or a radical of formula

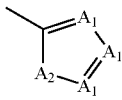

(c)

wherein each A$_1$ independently is N, CH or CR$^6$; and
A$_2$ is NH, O, S or NR$^6$.
(c-5) R$^3$ is C$_{1-6}$alkyl optionally substituted with cyano.

Also an interesting group of compounds are those compounds of formula (I) wherein R$^3$ is C$_{1-6}$alkyl optionally substituted with cyano.

A preferred subgroup is that wherein R$^2$ is cyano and R$^1$ is hydrogen.

Also an interesting group of compounds are those compounds of formula (I) wherein one or more, preferably all of the following restrictions apply:
(b-1) n is at least 1, in particular 1; or n is 0;
(b-2) R$^2$ is cyano;
(b-3) m is 1, 2 or 3;
(b-4) R$^4$ is C$_{1-6}$alkyl, especially methyl; halo;
(b-5) X$_1$ is NH or O;
(b-6) R$^1$ is hydrogen or C$_{1-4}$alkyl.

Interesting compounds are those compounds of formula (I) or any of the subgroups specified herein, wherein R$^4$ is halogen.

Another interesting group of compounds are those compounds of formula (I) or any of the subgroups specified herein, wherein R$^{17}$ is halo, cyano.

Another interesting group of compounds are those compounds of formula (I) or any of the subgroups specified herein, wherein R$^{17}$ is oxo, C$_{1-6}$alkyl optionally substituted with cyano, =N—O—C$_{1-6}$alkyl-Aryl, hydrogen, oxo, C$_{1-6}$alkyl optionally substituted with cyano or Het.

Another interesting group of compounds are those compounds of formula (I) or any of the subgroups specified herein, wherein m is 2 or 3 and X$_1$ is —NR$^5$—, —O—, —C(=O)—, —CH$_2$—, —CHOH—, —S—, —S(=O)$_p$—, in particular wherein X$_1$ is —NR$^5$—, or —O—.

Further subgroups of the compounds in accordance with the present invention are those compounds of formula (I) or any of the subgroups of compounds of formula (I) specified herein, wherein one or more of C$_{1-6}$alkyl is limited to C$_{1-4}$alkyl, one or more of C$_{1-4}$alkyl is limited to C$_{1-2}$alkyl; wherein one or more of C$_{2-6}$alkenyl is limited to C$_{2-4}$alkenyl; wherein one or more of C$_{2-6}$alkynyl is limited to C$_{2-4}$alkynyl.

Further subgroups of the compounds in accordance with the present invention are those compounds of formula (I) or any of the subgroups of compounds of formula (I) specified herein, wherein one or more of the radicals that are (or one or more of the radicals that contain) heterocycles or carbocycles are the heterocycles or carbocycles as specifically set forth therein.

Synthesis

The compounds of formula (I) can be prepared via a number of pathways a number of which are explained hereinafter in more detail.

The compounds of formula (I) can be generally prepared by reacting an intermediate of formula (a-1) with a pyrimidine or triazine derivative (a-2). The groups HX$_1$ and W$_1$ are selected such that a X$_1$ linking moiety is formed.

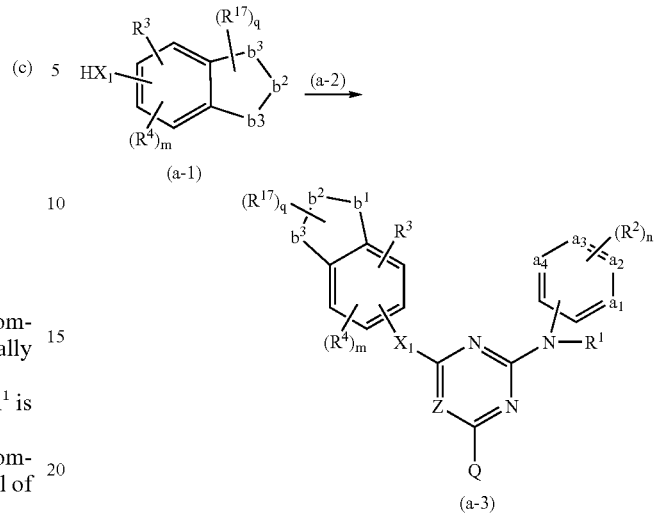

Reagent (a-2) is of general formula

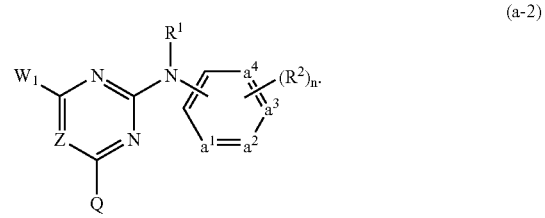

In particular, W$_1$ is a suitable leaving group and X$_1$ is a heteroatom. Examples of suitable leaving groups in (a-2) are halogen, in particular chloro and bromo, tosylate, mesylate, triflate and the like groups.

The conversion of (a-1) with (a-2) to (a-3) in the above scheme is particularly useful when W$_1$ is a leaving group and X$_1$ is a heteroatom such as —NR$^5$—, —NH—NH—, —N=N—, —O—, —S—, —X$_2$—C$_{1-4}$alkanediyl-. This conversion is particularly suited in the instance where X$_1$ is —O—. In the instance where is S, the latter can conveniently be transferred to the corresponding sulfoxide or sulfon using art-known oxidation procedures.

The above reaction usually is performed in the presence of a suitable solvent. Suitable solvents are for example acetonitrile, alcohols, such as for example ethanol, 2-propanol, ethylene glycol, propylene glycol, polar aprotic solvents such as N,N-dimethylformamide; N,N-dimethylacetamide, dimethylsufoxide, 1-methyl-2-pyrrolidinone, [bmim]PF$_5$; ethers such as 1,4-dioxane, propylene glycol monomethylether.

Where X$_1$ is —C(=O)— a starting material (a-1) wherein the group —X$_1$H is a Grignard type of group (—Mg-halo) or lithium is reacted with a starting material (a-2) wherein W$_1$ is an ester (—COOalkyl). The latter ester may also be reduced to an alcohol with e.g. LiAlH$_4$ and subsequently oxidized with a mild oxidant such as MnO$_2$ to the corresponding aldehyde which subsequently is reacted with the (a-1) starting material wherein the group —X$_1$H is a Grignard type of group (—Mg-halo) or lithium. The compounds wherein —X$_1$ is —C(=O)— can be converted to the —CHOH— analogs by a suitable reduction reaction e.g. with LiAlH$_4$.

Where $X_1$ is $C_{1-4}$alkanediyl the linkage can be introduced by a Grignard reaction, e.g. by reacting a starting material (a-1) wherein the —$X_1$H group is —$C_{1-4}$alkanediyl-Mg-halo with an (a-2) reagent wherein $W_1$ is a halo group, or vice versa. Where $X_1$ is methylene, the methylene group can be oxidized to a is —C(=O)— group ($X_1$ is —C(=O)—) e.g. with selenium dioxide. The —C(=O)— group in turn can be reduced with a suitable hydride such as LiAlH$_4$ to a —CHOH— group.

Where $X_1$ is —NR$^{13}$—C(=O)—, or —C(=O)—NR$^{13}$—, the $X_1$ linkage can be formed via a suitable amide bond forming reaction starting from an intermediate (a-1) wherein —$X_1$H is —NHR$^{13}$ and an intermediate (a-2) wherein W1 is a carboxyl group or an active derivative thereof, or vice versa starting from an intermediate (a-1) wherein —$X_1$H is carboxyl group or an active derivative thereof and an intermediate (a-2) wherein $W_1$ is a group —NHR$^{13}$. The amide bond formation may be done following methodologies generally known in the art, e.g. by activation of the carboxyl group to a carbonyl chloride or bromide or by using a suitable coupling agent.

Where $X_1$ is —$X_2$—$C_{1-4}$alkanediyl-, an intermediate (a-1) wherein —$X_1$H is —$X_2$H is reacted with an intermediate (a-2) wherein $W_1$ is —$C_{1-4}$alkanediyl-$W_2$, wherein $W_2$ in turn is a suitable leaving group. Or where $X_1$ is —$C_{1-4}$alkanediyl-$X_2$— an intermediate (a-1) wherein —$X_1$H is —$C_{1-4}$alkanediyl-$W_2$, wherein $W_2$ in turn is a suitable leaving group, is reacted with an intermediate (a-2) wherein $W_1$ is —$X_2$H.

The linkages of $X_2$ being other than a heteroatom (i.e. $X_2$ is —C(=O)—, —CHOH—) can be prepared in analogous procedures as for the linker $X_1$.

In the instance where $X_1$ is —NR$^5$— the reaction of (a-1) with reagent (a-2) is typically conducted under neutral conditions or, which is preferred, at acidic conditions, usually at elevated temperatures and under stirring. The acid conditions may be obtained by adding amounts of a suitable acid or by using acid solvents, e.g. hydrochloric acid dissolved in an alkanol such as 1- or 2-propanol.

The above reaction can be performed in the presence of a suitable solvent. Suitable solvents are for example acetonitrile, an alcohol, such as for example ethanol, 2-propanol, 2-propanol-HCl; N,N-dimethylformamide; N,N-dimethylacetamide, 1-methyl-2-pyrrolidinone; 1,4-dioxane, propyleneglycol monomethylether. Preferably the solvent is 2-propanol, 6 N HCl in 2-propanol or acetonitrile, especially acetonitrile. Optionally, sodium hydride may be present.

In the instance where $X_1$ is —O—, the reaction is typically conducted as follows. Intermediate (a-1) is first reacted under stirring at room temperature with hydrides in an organic solvent. Subsequently, a solvent, such as N-methylpyrrolidinone, dimethylacetamide or dimethylformamide, was added to the mixture and followed by the addition of reagent (a-2). Typically, the reaction mixture was stirred overnight at elevated temperatures to yield compound (a-3).

The compounds of formula (a-3) having a R$^{17}$ substituent which is an oxo (=O) group (represented by structure (a-3-1)) can be used as a starting material to obtain compounds of formula (I) having a R$^{17}$ substituent which is a =N—R$^{18}$ substituent, wherein =N—R$^{18}$ is =NH, =N—R$^{15}$, =N—R$^7$, =N—O—R$^{15}$, =N—O—R$^7$ as defined above. In this reaction pathway, intermediate (a-3-1) is reacted with reagent (a-7) (reagent (a-7 is of general formula NH$_3$, NH$_2$—R$^{15}$, NH$_2$—R$^7$, NH$_2$—O—R$^{15}$, NH$_2$—O—R$^7$, in particular Aryl-$C_{1-6}$alkyl-O—NH$_2$) at elevated temperatures in an alcoholic solvent in the presence of a base to generate a compound of formula (a-8).

Similarly, the compounds of formula (a-3-1) can be used as a starting material to obtain compounds of formula (I) having a R$^{17}$ substituent which is a =X substituent, wherein =X is =CH$_2$, =CH—C(=O)—NR$^{13}$R$^{14}$, =CH—R$^7$, or =CH—R$^{15}$ as defined above. Intermediate (a-3-1) is further reacted with reagent (a-4) in a Wittig reaction or a Wittig-Horner reaction. Reagent (a-4) is a Wittig type reagent, such as a triphenyl-phosphoniumylide, or a Wittig-Horner type of reagent, in particular a phosphonate, such as e.g. a reagent of formula di($C_{1-6}$alkyloxy)-P(=O)—$X_4$, wherein is $X_4$ is a substituent R$^{17}$ that can be linked to the ring via a double bond (exo double bond). The Wittig-Horner type of conversion typically is conducted in the presence of a base, preferably a strong base, in an aprotic organic solvent at room temperature. The reaction should be allowed sufficient time to complete, typically it is allowed to proceed overnight to yield compound (a-5). This latter compound may further be reacted in an alcoholic solvent under reducing conditions to generate a compound of formula (a-6).

Both conversion reactions are outlined in the following reaction scheme.

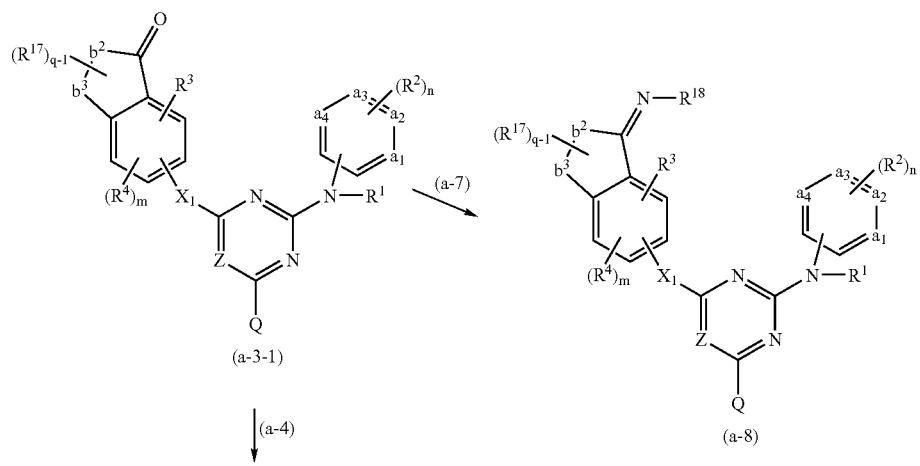

-continued

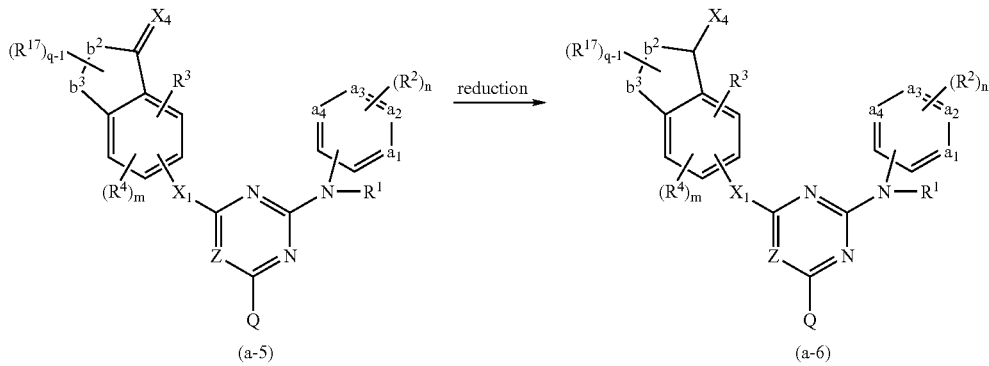

The oxo group in the compounds (a-3-1) may also be at other positions in the ring having the $R^{17}$ substituent(s), the same type of derivatisation may be done resulting in topical isomers of (a-8), (a-5) and (a-6).

The compounds of formula (I) can also be prepared as outlined in the reaction scheme here below.

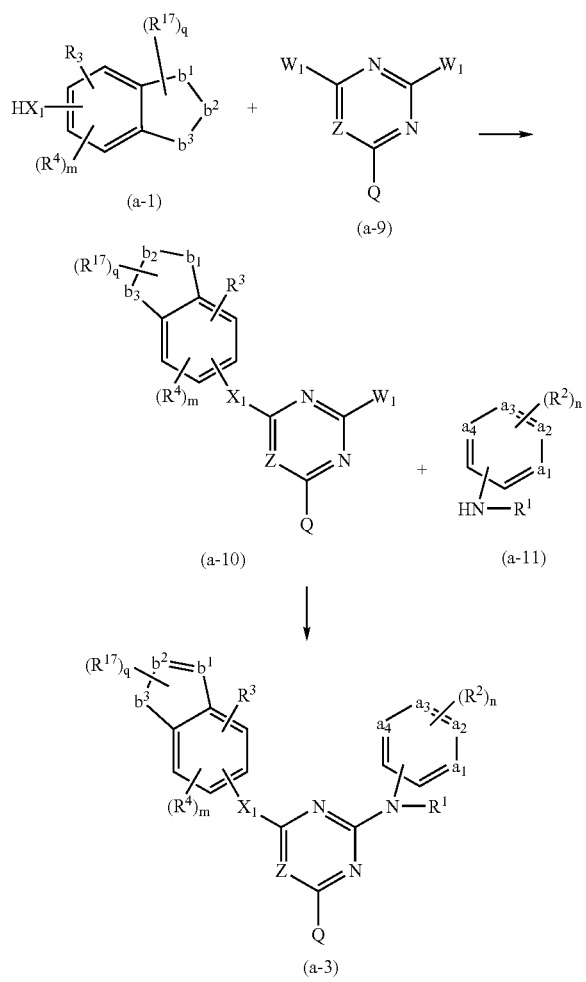

A reagent of formula (a-1) is reacted with a pyrimidine- or triazine derivative of formula (a-9) wherein the substituents have the meanings specified herein and $W_1$ is a suitable leaving group such as, for example, halo, triflate, tosylate, methylsulfonyl and the like, yielding an intermediate (a-10). This reaction can be done similarly as outlined above for the reaction of (a-1) with (a-2), in particular for the various possibilities of the linker —$X_1$—. Where necessary, the $W_1$ group that does not intervene in this reaction may be replaced by a leaving group precursor such as a OH functionality which a particular stage of the reaction procedure is converted to a leaving group, e.g. by converting the OH group into a halogen group, or by reacting it with a suitable reagent such as $POCl_3$, tosyl chloride, mesyl chloride and the like The end products (I) can be prepared from this starting material (a-10) by reaction with the amino substituted aromatic compound (a-11) in an arylation type of reaction.

Suitable solvents for the reaction of (a-1) with (a-9) and of (a-10) with (a-11) are ethers, e.g. 1,4-dioxane, THF, alcohols, ethanol, propanol, butanol, ethylene glycol, propylene glycol, propylene glycol monomethyl ether, the aprotic solvents such acetonitrile, DMF, DMA, 1-methyl-2-pyrrolidinone and the like. If necessary a base can be added. Suitable bases in this reaction are for example sodium acetate, potassium acetate, N,N-diethylethanamine, sodium hydrogencarbonate, sodium hydroxide and the like.

The compounds of formula (I) wherein $-b^1-b^2-b^3-$ is —$CH_2$—CH=CH— (b-5) can also be prepared starting from an indane derivative of formula (a-12) as outlined in the following scheme. Indane derivative (a-12) is converted to (a-13) using a Wittig or Wittig-Horner reaction similarly as outlined above. The conversion from (a-12) to (a-13) occurs similarly as described previously for the reaction of (a-3-1) to (a-5). $W_1$ and $HX_1$ are selected such that a $X_1$ linking moiety is formed. Product (a-13) subsequently is coupled with reagent (a-2).Preferably $W_1$ is a suitable leaving group and $X_1$ is a heteroatom. This reaction is performed using similar procedures as described above for the reaction of (a-1) with (a-2). $X_4$ has the same meaning as described above in the preparation of (a-5) and (a-6). In this coupling reaction two end products are obtained, on the one end a compound (a-14) on the other an isomer of (a-14) with $X_4$ being linked by an exo double bond.

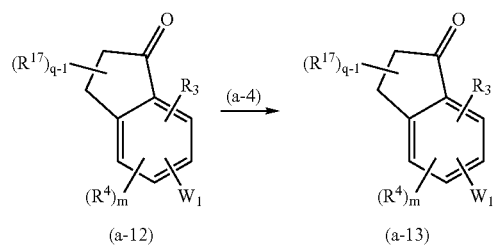

(a-12) → (a-13) +

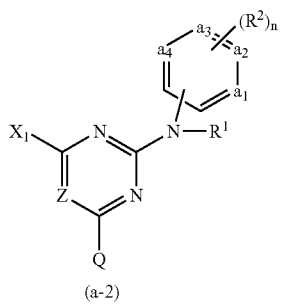

(a-2)

↓

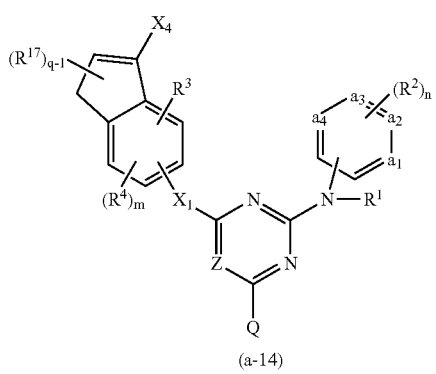

(a-14)

The compounds of formula (I) wherein -b$^1$-b$^2$-b$^3$- is —CH$_2$—CH=CH— (b-5) can also be prepared starting from an indane derivative of formula (a-16) as outlined in the following scheme.

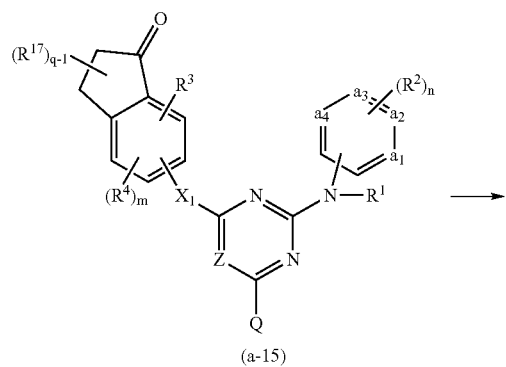

(a-15)

-continued

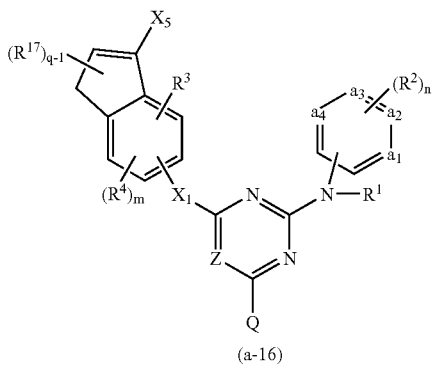

(a-16)

In this alternative pathway intermediate (a-15) is reacted with a suitable halogenating agent e.g. with phosphorous oxychloride to generate a compound of formula (a-16), wherein X$^5$ is halo. Typically this reaction is conducted overnight at elevated temperatures. Intermediate (a-15) can also be reacted with a bromo derivative such as PBr$_5$.

The compounds of formula (I) wherein Z is N (triazines) can also be prepared by a triazine forming condensation reactions as described e.g in EP-A-834 507. Triazine derivatives of formula (I) wherein radical Q is NR$^9$R$^{10}$ can be prepared by reacting a triazine compound of formula (I) wherein Q is halo, in particular wherin Q is chloro or bromo, with an amine H—NR$^9$R$^{10}$ following art-known procedures.

In this and the following preparations, the reaction products may be isolated from the reaction medium and, if necessary, further purified according to methodologies generally known in the art such as, for example, extraction, crystallization, distillation, trituration and chromatography.

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-.butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, a compound of formula (I) wherein R$^3$ comprises cyano, can be converted into a compound of formula (I) wherein R$^3$ comprises aminocarbonyl, by reaction with HCOOH, in the presence of a suitable acid, such as hydrochloric acid. A compound of formula (I) wherein R$^3$ comprises cyano, can also further be converted into a compound of formula (I) wherein R$^3$ comprises tetrazolyl, by reaction with sodium azide in the presence of ammonium chloride and N,N-dimethylacetamide.

Compounds of formula (I) wherein $R^3$ comprises aminocarbonyl, can be converted into a compound of formula (I) wherein $R^3$ comprises cyano, in the presence of a suitable dehydrating agent. The dehydration can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, $TsCl$, $P_2O_5$, $(Ph_3PO_3SCF_3)$ $O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3, COCl_2$, $NaCl.AlCl_3$, $ClCOCOCl$, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiMe_2)_4$, $LiAlH_4$ and the like. All the reagents listed in said publication are incorporated herein as reference.

Compounds of formula (I) wherein $R^3$ comprises $C_{2-6}$alkenyl can be converted into a compound of formula (I) wherein $R^3$ comprises $C_{1-6}$alkyl by reduction in the presence of a suitable reducing agent, such as for example $H_2$, in the presence of a suitable catalyst, such as for example palladium on charcoal, and in the presence of a suitable solvent, such as for example an alcohol, e.g. methanol.

Compounds of formula (I) wherein $R^3$ represents $CH(OH)$—$R^{16}$, can be converted into a compound of formula (I) wherein $R^3$ represents $C(=O)$—$R^{16}$ by reaction with Jones's reagent in the presence of a suitable solvent, such as for example 2-propanone.

Compound of formula (I) wherein $R^3$ represents $C(=O)$—$CH_2$—$R^{16a}$, wherein $R^{16a}$ represents cyano or aminocarbonyl, can be converted into a compound of formula (I) wherein $R^3$ represents $C(Cl)=CH$—$R^{16a}$ by reaction with $POCl_3$.

Compounds of formula (I) wherein $R^3$ represents a monocyclic, bicyclic or tricyclic saturated, partially saturated or aromatic carbocycle or a monocyclic, bicyclic or tricyclic saturated, partially saturated or aromatic heterocycle substituted with formyl can be converted into compounds of formula (I) wherein $R^3$ represents a monocyclic, bicyclic or tricyclic saturated, partially saturated or aromatic carbocycle or a monocyclic, bicyclic or tricyclic saturated, partially saturated or aromatic heterocycle substituted with $CH(=N$—$O$—$R^8)$ by reaction with $NH_2OR^8$ in the presence of a suitable base, such as for example sodium hydroxide and a suitable solvent, such as for example an alcohol, e.g. ethanol and the like. Compounds of formula (I) wherein $R^3$ represents a monocyclic, bicyclic or tricyclic saturated, partially saturated or aromatic carbocycle or a monocyclic, bicyclic or tricyclic saturated, partially saturated or aromatic heterocycle substituted with $CH(=N$—$O$—$R^8)$ can be converted into a compound of formula (I) wherein $R^3$ represents a monocyclic, bicyclic or tricyclic saturated, partially saturated or aromatic carbocycle or a monocyclic, bicyclic or tricyclic saturated, partially saturated or aromatic heterocycle substituted with CN by reaction with a carbodiimide in the presence of a suitable solvent, such as for example tetrahydrofuran.

Compounds of formula (I) wherein $R^4$ represents nitro, can be converted into a compound of formula (I) wherein $R^4$ is amino, in the presence of a suitable reducing agent, such as for example $H_2$, in the presence of a suitable catalyst, such as for example Raney Nickel, and in the presence of a suitable solvent, such as for example an alcohol, e.g. methanol.

Compounds of formula (I) wherein $R^1$ is hydrogen, can be converted into a compound of formula (I) wherein $R^1$ is $C_{1-6}$alkyl, by reaction with a suitable alkylating agent, such as for example iodo-$C_{1-6}$alkyl, in the presence of a suitable base, such as for example sodium hydride, and a suitable solvent, such as for example tetrahydrofuran.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures or some of the compounds of formula (I) or the described intermediates may be prepared according to the procedures described in WO 99/50250 and WO 00/27825.

Intermediates of formula (a-2) can be prepared by reacting an intermediate of formula (b-1) with a leaving group introducing agent of formula (b-2) wherein $W_1$ represents the leaving group and R represents the remaining of the leaving group introducing agent, such as for example $POCl_3$.

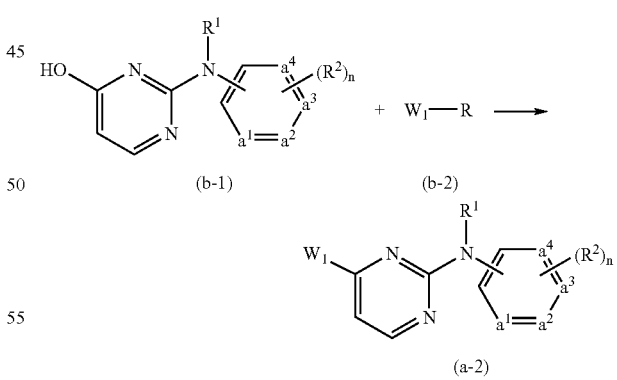

Suitable leaving groups in the above reaction are for example halo, triflate, tosylate, mesylate and the like. Preferably, $W_1$ is halo, more preferably iodo or bromo.

Suitable bases in the above reaction are for example sodium acetate, potassium acetate, N,N-diethylethanamine, sodium hydrogencarbonate, sodium hydroxide and the like.

Suitable solvents in the above reaction are for example acetonitrile, N,N-dimethylacetamide, an ionic liquid e.g.

[bmim]PF$_6$, N,N-dimethylformamide, water, tetrahydrofuran, dimethylsulphoxide, 1-methyl-2-pyrrolidinone and the like.

Compounds of formula (I) having a carbon-carbon double bond can be reduced to the corresponding compounds with a single bond using catalytic hydrogenation procedures. In these procedures use is made of a noble metal catalyst. An attractive such catalyst is Pd. The palladium (Pd) catalyst may be a homogeneous Pd catalyst, such as for example Pd(OAc)$_2$, PdCl$_2$, Pd(PPh$_3$)$_4$, Pd(PPh$_3$)$_2$Cl$_2$, bis(dibenzylidene acetone)palladium, palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' 2$^{nd}$ edition, T W Greene & P G M Wutz, Wiley Interscience (1991).

The compounds of formula (I) show antiretroviral properties (reverse transcriptase inhibiting properties), in particular against Human Immunodeficiency Virus (HIV), which is the etiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

In another aspect, the present invention also provides pharmaceutical compositions comprising a therapeutically effective amount of a compound of formula (I) and a pharmaceutically acceptable carrier or diluent. In still a further aspect there is provided a method of preparation a pharmaceutical composition as specified herein comprising mixing a compound of formula (I) with a suitable pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components ( in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting-under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder.

The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness.

Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in the prevention or treatment of retroviral infections, in particular, in the treatment of infections with multi-drug resistant retroviruses. Thus, to combat, prevent or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, RPR 103611, YK-FH312, IC 9564, 5-helix, D-peptide ADS-J1; co-receptor binding inhibitors, such as, for example, AMD 3100, AMD-3465, AMD7049, AMD3451 (Bicyclams), TAK 779, T-22, ALX40-4C; SHC-C (SCH351125), SHC-D, PRO-140, RPR103611; RT inhibitors, such as, for example, foscarnet and prodrugs; nucleoside RTIs, such as, for example, AZT, 3TC, DDC, DDI, D4T, Abacavir, FTC, DAPD (Amdoxovir), dOTC (BCH-10652), fozivudine, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, QM96521, GW420867X, DPC 961, DPC963, DPC082, DPC083, TMC-125, calanolide A, SJ-3366, TSAO, 4"-deaminated TSAO, MV150, MV026048, PNU-142721; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908 (fosamprenavir), ritonavir, nelfinavir, saquinavir, indinavir, lopinavir, palinavir, BMS 186316, atazanavir, DPC 681, DPC 684, tipranavir, AG1776, mozenavir, DMP-323, GS3333, KNI-413, KNI-272, L754394, L756425, LG-71350, PD161374, PD173606, PD177298, PD178390, PD178392, PNU 140135, TMC-114, maslinic acid, U-140690; glycosylation inhibitors, such as, for example, castanospermine, deoxynojirimycine; entry inhibitors CGP64222.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

EXAMPLES

The following examples are intended to illustrate the present invention.

Hereinafter, "DMF" is defined as N,N-dimethylformamide, "DIPE" is defined as diisopropyl ether, "THF" is defined as tetrahydrofurane, "DMSO" is defined as dimethylsulfoxide, "EtOAc" is defined as ethylacetate, "pyr" is defined as pyridine.

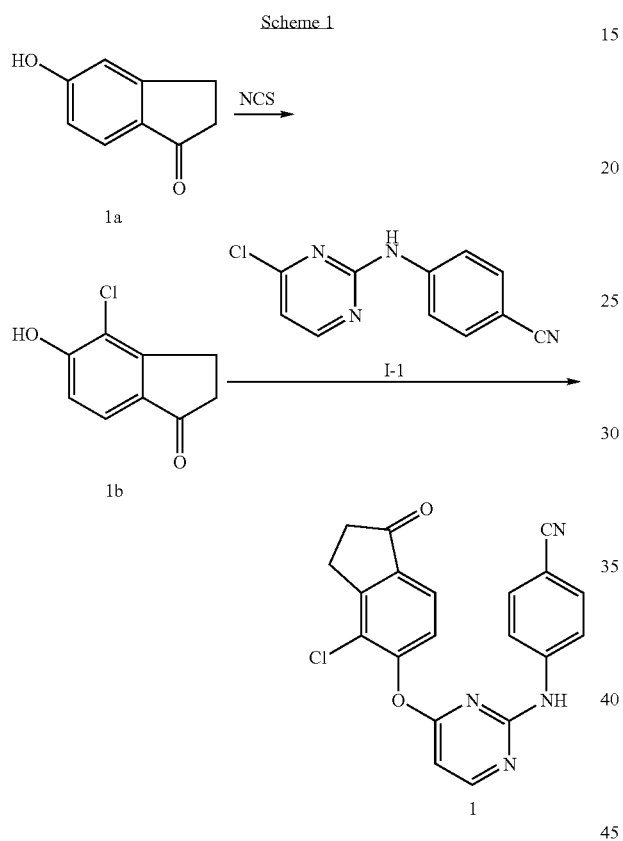

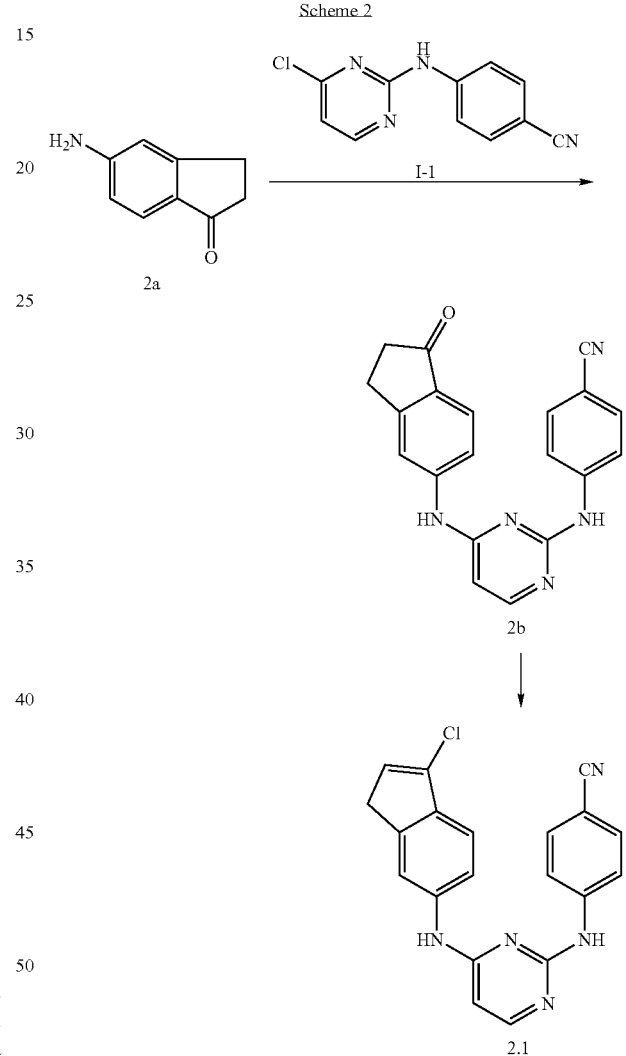

Example 1

Preparation of Intermediate 1b

N-Chlorosuccinimide (NCS) (0.025 mol) was added portionwise to a mixture of 5-hydroxy-1-indanone 1a (0.022 mol) in acetonitrile (60 ml). The mixture was stirred and refluxed overnight. $H_2O$ was added and the mixture was extracted with $CH_2Cl_2$. The organic layer was separated, dried with $MgSO_4$, filtered, and evaporated. The residue (6 g) was purified by column chromatography over silica gel (eluent: cyclohexane/EtOAc 60/40; 15-40 μm). Two fractions were collected and evaporated, yielding: 2.2 g F1 and 1.3 g of starting material. F1 was crystallized from di-isopropyl ether. The precipitate was filtered off and dried yielding 0.9 g of intermediate 1b (22%) (Melting point: 212° C.)

Example 2

Sodium hydride (60% in oil) (0.0054 mol) was added to a mixture of 1b (0.0049 mol) in 1,4-dioxane (10 ml). The mixture was stirred for 10 minutes. 1-methylpyrrolidinone (10 ml) was added. The mixture was stirred for 10 minutes. Intermediate I-1 (0.0049 mol) was added. The mixture was stirred at 140° C. overnight. $H_2O$ was added. The mixture was extracted with $CH_2Cl_2$. The organic layer was washed with $K_2CO_3$ 10%, dried ($MgSO_4$), filtered and the solvent was evaporated. Yielding: 1.6 g of residue. This fraction was crystallized from $CH_3CN$. The precipitate was filtered off and dried. Yielding: 0.46 g of compound 1 (29%). Melting point: >260° C. (MH+): (388)

Example 3

A mixture of 5-amino-indan-1-one (0.0003 mol) and intermediate I-1 (0.0003 mol) in HCl 3N (2 ml) was stirred and refluxed for 2 hours. The precipitate was filtered, washed with $H_2O$ and diisopropyl ether and dried. The yield of this procedure was 0.06 g (52%). This fraction was crystallized from CH3CN/diisopropyl ether. The precipitate was filtered off and dried, yielding 0.035 g of intermediate 2b (30%). (Melting point: >260° C.)

Example 4

Preparation of Compound 2.1

A mixture of intermediate 2b (0.0012 mol) in POCl₃ (1 ml) was stirred and refluxed overnight. The solvent was evaporated till dryness. The residue was taken up in K₂CO₃ 10%. The mixture was extracted with CH₂Cl₂. The organic layer was separated, dried (MgSO₄), filtered, and evaporated. The residue (0.73 g) was purified by column chromatography over kromasil (eluent: CH₂Cl₂/CH₃OH 99/1; 5 μm). Two fractions were collected and the solvent was evaporated yielding 0.08 g F1 (17%) and 0.14 g F2 (33%). F1 was crystallized from CH₃CN/di-isopropyl ether. The precipitate was filtered off and dried. The yield of compound 2.1 is 0.038 g. (Melting point>270° C.; (MH+): 370).

Examples 5-8

Synthesis of Further Indene-Substituted 2,6-Diaminopyrimidines

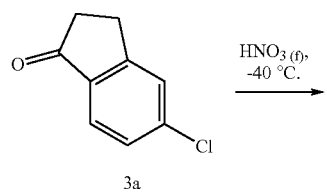

3a

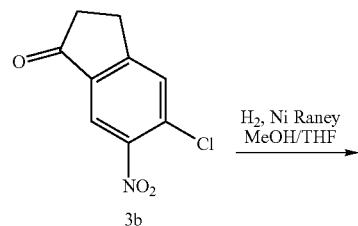

3b

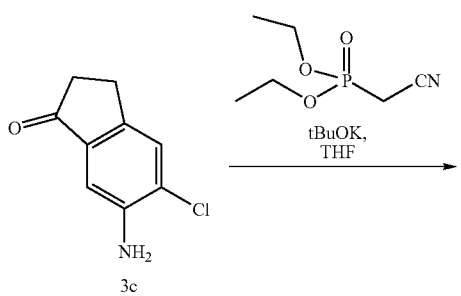

3c

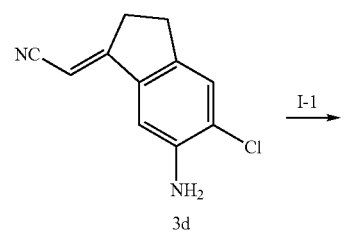

3d

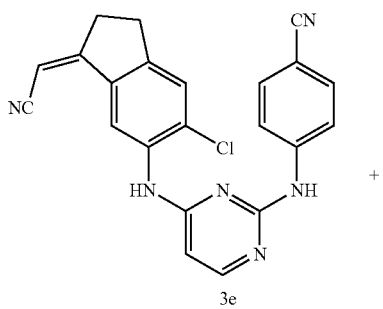

3e

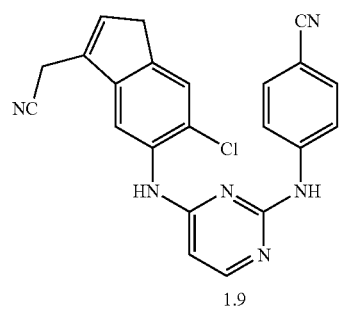

1.9

Example 5

Preparation of Intermediate 3b

Fuming nitric acid (0.362 mol) was added at −40° C. to 5-chloro-1-indanone (intermediate 3a, 26.7 mmol). The mixture was stirred for two hours at −40° C. It was then poured onto ice and extracted with dichloromethane. The organic layer was separated, washed with brine, dried with MgSO₄, filtered and evaporated. The residue was purified by column chromatography over silica gel (eluent: cyclohexane/AcOEt 65/35; 15-40 μm). The pure fractions were collected and the solvent evaporated yielding 4.15 g of intermediate 3b (73%). (Melting Point: 129° C.)

Example 6

Preparation of Intermediate 3c

In a Parr hydrogenation apparatus, 0.5 g of Raney Nickel was added to a solution of intermediate 3b (8.60 mmol) in a mixture of THF and MeOH (6/1). The vessel was flushed with nitrogen and put under an hydrogen atmosphere (3 bars). The mixture was stirred for one hour at room temperature, filtered over celite and evaporated to dryness to yield 1.50 g of intermediate 3c (96%). (Melting Point: 214° C.)

Example 7

Preparation of Intermediate 3d (E/Z=89/11)

Potassium tert-butoxide (56.4 mmol) was added portionwise at 0° C. to a solution of cyanomethylphosphonate (56.4 mmol) in THF. The mixture was stirred for 15 min at 15° C.

Then a solution of intermediate 3c (14.1 mmol) in THF was added dropwise at 0° C. The reaction mixture was stirred at room temperature overnight, poured onto water, acidified with 3M hydrochloric acid and extracted with dichloromethane. The organic layer was separated, washed with a 10% solution of potassium carbonate, with brine, dried over magnesium sulfate, filtered and evaporated. The residue was purified by column chromatography over silica gel (eluent : dichloromethane; 35-70 µm). The pure fractions were collected and the solvent evaporated yielding 1.88 g of intermediate 3d (65 %). (Melting Point: 196° C.)

Example 8

Preparation of Compound 1.9 and 3e (Z 100%)

Intermediates 3d and I-1 were intimately ground together and fused with a heating gun. The residue was taken up with a 90/10 mixture of dichloromethane and methanol and with a 10% solution of potassium carbonate. The organic layer was separated, washed with a brine solution, dried over magnesium sulfate, filtered and evaporated. The residue was purified by column chromatography over silica gel (eluent : dichloromethane/AcOEt 85/15; 15-40 µm). Two fractions were collected and evaporated yielding 0.126 g of an isomer 3e (13%) and 0.104g of compound 1.9 (11%). Each fraction was recrystallized in acetonitrile yielding an isomer 3e (Melting Point: 248-249° C.) and compound 1.9 (Melting point>250° C).

Examples 9-11

Synthesis of 2-amino-4-benzofuran Substituted Pyrimidines

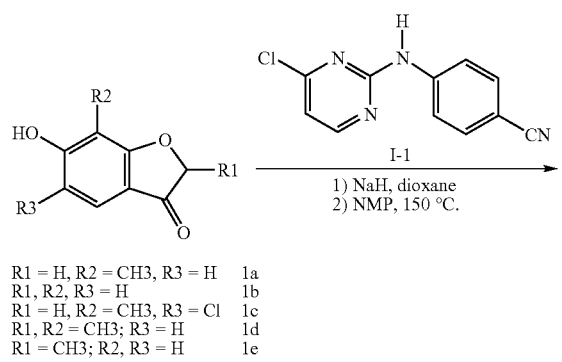

R1 = H, R2 = CH3, R3 = H    1a
R1, R2, R3 = H              1b
R1 = H, R2 = CH3, R3 = Cl   1c
R1, R2 = CH3; R3 = H        1d
R1 = CH3; R2, R3 = H        1e

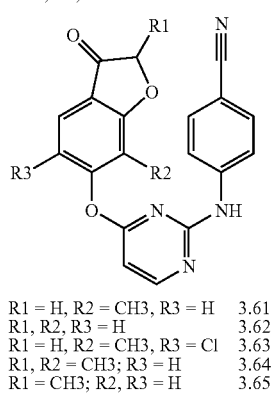

R1 = H, R2 = CH3, R3 = H    3.61
R1, R2, R3 = H              3.62
R1 = H, R2 = CH3, R3 = Cl   3.63
R1, R2 = CH3; R3 = H        3.64
R1 = CH3; R2, R3 = H        3.65

-continued

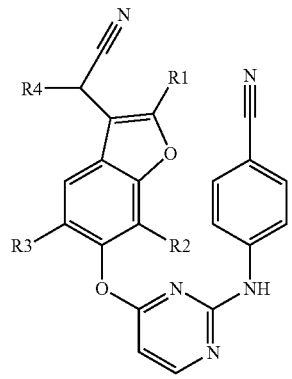

R1 = H, R2 = CH3, R3, R4 = H        3.1
R1, R3, R2, R4 = H                  3.2
R1 = H, R2 = CH3, R3 = Cl, R4 = H   3.3
R1, R2 = CH3; R3, R4 = H            3.19
R1 = CH3; R2, R3, R4 = CH3          3.20
R1, R3, R2 = H, R4 = CH3            3.4
R1, R3 = H; R2, R4 = CH3            3.5
R1 = H, R2, R4 = CH3, R3 = Cl       3.6

Example 9

Preparation of Compound 3.61

Sodium hydride (60% in oil) (0.0134 mol) was added to a mixture of 1a (0.0122 mol) in 1,4-dioxane (20 ml). The mixture was stirred for 10 minutes. 1-methylpyrrolidinone (20 ml) was added and stirred for 10 minutes. Reagent I-1 was added (0.0122 mol) to the mixture and the mixture was stirred at 140° C. overnight. $H_2O$ was added to the mixture, after which the mixture was extracted with $CH_2Cl_2/CH_3OH$. The organic layer was washed with $K_2CO_3$ 10%, dried with $MgSO_4$, filtered, and finally evaporated. The residue was purified by column chromatography over silica gel (eluent: $CH_2Cl_2/CH_3OH$ 99/1; 15-40 µm). Two fractions were collected and evaporated. The two fractions yielding respectively 0.271 g F1 (6%), 0.74 g F2 (secondary product). 0.1 g of F1 was crystallized from di-isopropyl ether/$CH_3CN$. The precipitate was filtered and dried. The overall yield of die synthesis procedure is 0.034 g of compound 3.61. (Melting point: 253° C., (MH+): 359)

Example 10

Preparation of Compound 3.62

Sodium hydride (60% in oil) (0.027 mol) was added to a solution of 1b (0.027 mol) in 1,4-dioxane(40 ml). The mixture was stirred at room temperature for 15 minutes. 1-methylpyrrolidinone (30 ml) was added and the mixture was stirred for 10 minutes, after which reagent I-1 (0.027 mol) was added. The mixture was stirred at 140° C. overnight, poured into $H_2O$ and extracted with $CH_2Cl_2$. The organic layer was separated, dried with $MgSO_4$, subsequently filtered, and the solvent was evaporated. The residue (9 g) was purified by column chromatography over silica gel (eluent: cyclohexane/EtOAc 70/30; 20-45 μm). The fractions were collected and the solvent was evaporated. The yield was 0.6 g (9%). This fraction, containing compound 3.62 was crystallized from CH₃OH. The precipitate was filtered off and dried, yielding: 0.044 g of compound 3.62. (Melting point: >260° C.; (MH+): 345)

The compounds of formula 3.63 to 3.65 are prepared according to the procedures of Example 9 and 10

Example 11

Preparation of Compound 3.1

Sodium hydride (60% in oil) (0.0008 mol) was added at 5° C. to a mixture of diethyl cyanomethylphosphonate (0.0008 mol) in THF (13 ml) under N₂ flow. The mixture was stirred. Compound 3.61 (0.0005 mol) was added. The mixture was stirred at room temperature overnight, poured out into H₂O and extracted with CH₂Cl₂. The organic layer was separated, dried (MgSO₄), filtered, and evaporated. The residue (0.23 g) was purified by column chromatography over silica gel (eluent: CH₂Cl₂ 100; 15-40 μm). The fractions containing compound 3.1 were collected and evaporated (yield: 0.1 g). This fraction was crystallized from diisopropyl ether/CH₃CN. The precipitate was filtered off and dried, yielding 0.058 g of compound 3.1 (26%). (Melting point: 226° C.; (MH+): 382)

Example 12

Preparation of Compound 3.2

Potassium ter-butoxide (0.0013 mol) was added at 5° C. to a solution of diethyl cyanomethylphosphonate (0.0013 mol) in THF (5 ml) under N₂ flow. The mixture was stirred at room temperature for 1 hour. A mixture of compound 3.62 (0.0008 mol) in THF (5 ml) was added. The mixture was stirred at room temperature for 1 hour. H₂O was added and subsequently extracted with CH₂Cl₂. The organic layer was separated, dried (MgSO₄), filtered, and evaporated (yielding: 0.3 g (93%)). The fraction containing compound 3.2 was crystallized from CH₃OH/CH₂Cl₂. The precipitate was filtered off and dried, yielding: 0.045 g of compound 3.2 (14%). (Melting point: 227° C.; (MH+): 368)

The compounds of formula 3.3-3.6 and 3.19-3.20 are prepared according to the above scheme of Examples 11 or 12.

Synthesis of compounds 4.8-4.11

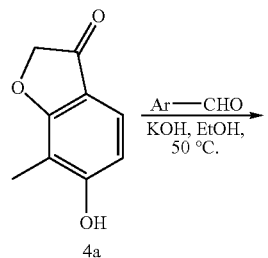

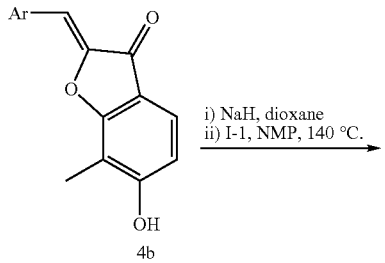

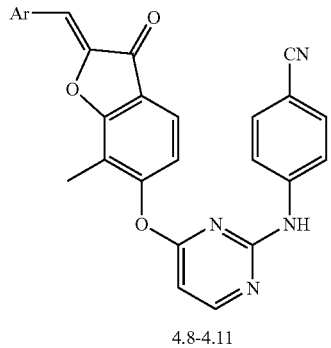

Example 13

Preparation of Intermediate 4b-1

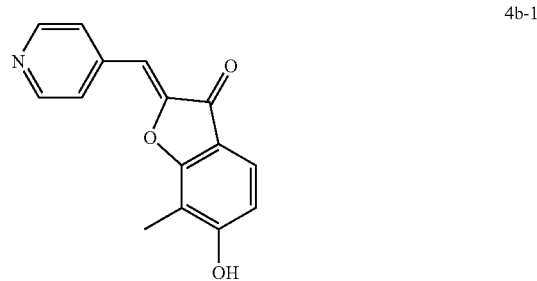

Compound 4a (12.2 mmol) was mixed with 4-pyridinecarboxaldehyde (13.4 mmol) in ethanol. Potassium hydroxide (97.6 mmol) was added and the reaction mixture was stirred for two hours at 50° C. The precipitate was filtered. The mother liquor was evaporated to dryness. The precipitate and the evaporation residue were taken up in water and acidified with 3M hydrochloric acid. The precipitate was filtered and dried yielding 2.59 g (84%) of intermediate 4b-1. (Melting point>260° C.)

Example 14

Preparation of Compounds 4.8-4.11

Compounds 4.8, 4.9, 4.10 and 4.11, were synthesized according to the procedure described in example 2 but using an intermediate 4b as starting material.

| No. | Ar— | Physical Data |
|---|---|---|
| 4.8 | phenyl | |
| 4.9 | pyridin-2-yl | Mp > 260° C. |
| 4.8 | phenyl | |
| 4.10 | pyridin-3-yl | Mp > 260° C. |
| 4.11 | pyridin-4-yl | Mp > 260° C. |

The compounds listed in the following tables can be prepared in accordance with the procedures of the above examples or obvious equivalents thereof.

TABLE 1

| N° | X¹ | R$^{17a}$ | R$^{17b}$ | R$^{17c}$ | R³ | R⁴ | Y | Q |
|---|---|---|---|---|---|---|---|---|
| 1.1 | NH | —Cl | H | H | H | H | H | H |
| 1.2 | NH | —Br | H | H | H | H | H | H |
| 1.3 | NH | —CN | H | H | H | H | H | H |
| 1.4 | NH | —CH=CH—CN | H | H | H | H | H | H |

TABLE 1-continued

| N° | X¹ | R$^{17a}$ | R$^{17b}$ | R$^{17c}$ | R³ | R⁴ | Y | Q |
|---|---|---|---|---|---|---|---|---|
| 1.5 | NH | —CN | H | H | Cl | H | H | H |
| 1.6 | NH | —CN | H | H | CH₃ | CH₃ | H | H |
| 1.7 | O | —CN | H | H | CH₃ | CH₃ | H | H |
| 1.8 | O | —CN | H | H | Cl | H | H | H |
| 1.9 | NH | —CH₂—CN | H | H | Cl | H | H | H |
| 1.10 | O | —CH₂—CN | H | H | Cl | H | H | H |
| 1.11 | NH | —CH₂—CN | H | H | CH₃ | CH₃ | H | H |
| 1.12 | O | —CH₂—CN | H | H | CH₃ | CH₃ | H | H |

TABLE 2

| N° | X¹ | R$^{17a}$ | R$^{17b}$ | R$^{17c}$ | R³ | R⁴ | Y | Q |
|---|---|---|---|---|---|---|---|---|
| 2.1 | NH | —Cl | H | H | H | H | H | H |
| 2.2 | NH | —Br | H | H | H | H | H | H |
| 2.3 | NH | —CN | H | H | H | H | H | H |
| 2.4 | NH | —CH=CH—CN | H | H | H | H | H | H |
| 2.5 | NH | —CN | H | H | Cl | H | H | H |
| 2.6 | NH | —CN | H | H | CH₃ | CH₃ | H | H |
| 2.7 | O | —CN | H | H | CH₃ | CH₃ | H | H |
| 2.8 | O | —CN | H | H | Cl | H | H | H |

TABLE 3

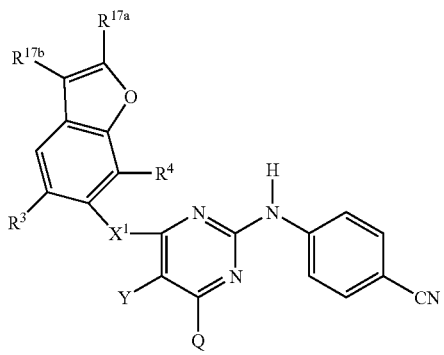

| N° | X¹ | R$^{17a}$ | R⁴ | R³ | Y | Q | R$^{17b}$ |
|---|---|---|---|---|---|---|---|
| 3.1 | O | H | CH₃ | H | H | H | —CH₂CN |
| 3.2 | O | H | H | H | H | H | —CH₂CN |
| 3.3 | O | H | CH₃ | Cl | H | H | —CH₂CN |
| 3.4 | O | H | H | H | H | H | —CH(CH₃)—CN |
| 3.5 | O | H | CH₃ | H | H | H | —CH(CH₃)—CN |
| 3.6 | O | H | CH₃ | Cl | H | H | —CH(CH₃)—CN |
| 3.7 | O | H | H | H | H | H | —CN |
| 3.8 | O | H | CH₃ | H | H | H | —CN |
| 3.9 | O | H | CH₃ | Cl | H | H | —CN |
| 3.10 | NH | H | CH₃ | H | H | H | —CH₂CN |
| 3.11 | NH | H | H | H | H | H | —CH₂CN |
| 3.12 | NH | H | CH₃ | Cl | H | H | —CH₂CN |
| 3.13 | NH | H | H | H | H | H | —CH(CH₃)—CN |
| 3.14 | NH | H | CH₃ | H | H | H | —CH(CH₃)—CN |
| 3.15 | NH | H | CH₃ | Cl | H | H | —CH(CH₃)—CN |
| 3.16 | NH | H | H | H | H | H | —CN |
| 3.17 | NH | H | CH₃ | H | H | H | —CN |
| 3.18 | NH | H | CH₃ | Cl | H | H | —CN |
| 3.19 | O | CH₃ | CH₃ | H | H | H | —CH₂CN |
| 3.20 | O | CH₃ | H | H | H | H | —CH₂CN |
| 3.21 | N | CH₃ | CH₃ | H | H | H | —CH₂CN |
| 3.22 | N | CH | H | H | H | H | —CH₂CN |
| 3.23 | O | H | H | H | H | H | CH₂-(2)Pyr |
| 3.24 | O | H | CH₃ | H | H | H | CH₂-(2)Pyr |
| 3.25 | O | H | CH₃ | Cl | H | H | CH₂-(2)Pyr |
| 3.26 | O | H | H | H | H | H | CH₂-(3)Pyr |
| 3.27 | O | H | CH₃ | H | H | H | CH₂-(3)Pyr |
| 3.28 | O | H | CH₃ | Cl | H | H | CH₂-(3)Pyr |
| 3.29 | NH | H | H | H | H | H | CH₂-(2)Pyr |
| 3.30 | NH | H | CH₃ | H | H | H | CH₂-(2)Pyr |
| 3.31 | NH | H | CH₃ | Cl | H | H | CH₂-(2)Pyr |
| 3.32 | NH | H | H | H | H | H | CH₂-(3)Pyr |
| 3.33 | NH | H | CH₃ | H | H | H | CH₂-(3)Pyr |
| 3.34 | NH | H | CH₃ | Cl | H | H | CH₂-(3)Pyr |
| 3.35 | O | H | CH₃ | H | H | CH₃ | CH₂—CN |
| 3.36 | O | H | H | H | H | CH₃ | CH₂—CN |
| 3.37 | O | H | H | H | H | CH₃ | CH(CH₃)—CN |
| 3.38 | O | H | CH₃ | H | H | CH₃ | CH(CH₃)—CN |
| 3.39 | O | H | CH₃ | Cl | H | CH₃ | CH₂—CN |
| 3.40 | O | H | CH₃ | Cl | H | CH₃ | CH(CH₃)—CN |
| 3.41 | NH | H | CH₃ | H | H | CH₃ | CH₂—CN |
| 3.42 | NH | H | H | H | H | CH₃ | CH₂—CN |
| 3.43 | NH | H | H | H | H | CH₃ | CH(CH₃)—CN |
| 3.44 | NH | H | CH₃ | H | H | CH₃ | CH(CH₃)—CN |
| 3.45 | NH | H | CH₃ | Cl | H | CH₃ | CH₂—CN |
| 3.46 | NH | H | CH₃ | Cl | H | CH₃ | CH(CH₃)—CN |
| 3.47 | O | H | CH₃ | H | Br | H | CH₂—CN |
| 3.48 | O | H | H | H | Br | H | CH₂—CN |
| 3.49 | O | H | H | H | Br | H | CH(CH₃)—CN |
| 3.50 | O | H | CH₃ | H | Br | H | CH(CH₃)—CN |
| 3.51 | O | H | CH₃ | Cl | Br | H | CH₂—CN |
| 3.52 | O | H | CH₃ | Cl | Br | H | CH(CH₃)—CN |
| 3.53 | NH | H | CH₃ | H | Br | H | CH₂—CN |
| 3.54 | NH | H | H | H | Br | H | CH₂—CN |
| 3.55 | NH | H | H | H | Br | H | CH(CH₃)—CN |
| 3.56 | NH | H | CH₃ | H | Br | H | CH(CH₃)—CN |
| 3.57 | NH | H | CH₃ | Cl | Br | H | CH₂—CN |
| 3.58 | NH | H | CH₃ | Cl | Br | H | CH(CH₃)—CN |
| 3.59 | O | H | H | CH₃ | H | H | CH(CH₃)CN |
| 3.60 | O | H | CH₃ | CH₃ | H | H | CH(CH₃)CN |

TABLE 4

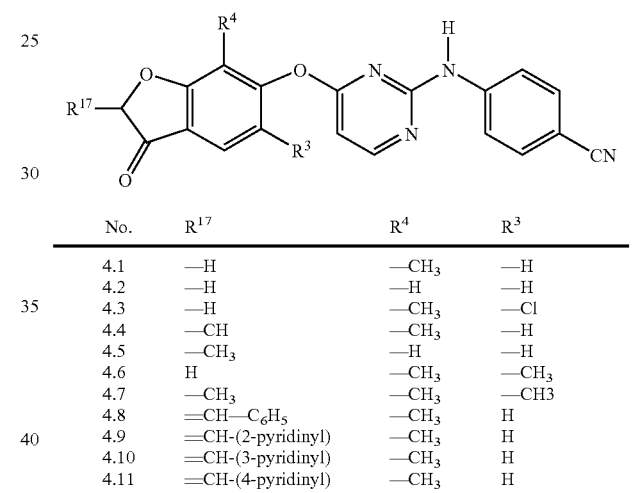

| No. | R$^{17}$ | R⁴ | R³ |
|---|---|---|---|
| 4.1 | —H | —CH₃ | —H |
| 4.2 | —H | —H | —H |
| 4.3 | —H | —CH₃ | —Cl |
| 4.4 | —CH | —CH₃ | —H |
| 4.5 | —CH₃ | —H | —H |
| 4.6 | H | —CH₃ | —CH₃ |
| 4.7 | —CH₃ | —CH₃ | —CH3 |
| 4.8 | =CH—C₆H₅ | —CH₃ | H |
| 4.9 | =CH-(2-pyridinyl) | —CH₃ | H |
| 4.10 | =CH-(3-pyridinyl) | —CH₃ | H |
| 4.11 | =CH-(4-pyridinyl) | —CH₃ | H |

TABLE 5

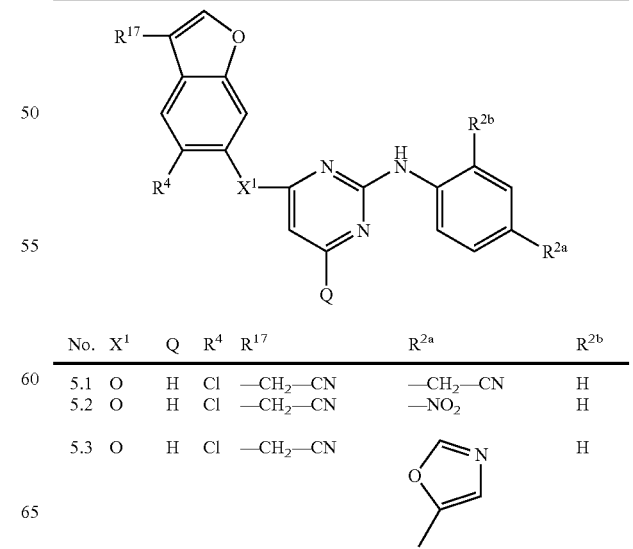

| No. | X¹ | Q | R⁴ | R$^{17}$ | R$^{2a}$ | R$^{2b}$ |
|---|---|---|---|---|---|---|
| 5.1 | O | H | Cl | —CH₂—CN | —CH₂—CN | H |
| 5.2 | O | H | Cl | —CH₂—CN | —NO₂ | H |
| 5.3 | O | H | Cl | —CH₂—CN | 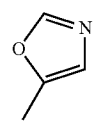 | H |

TABLE 5-continued

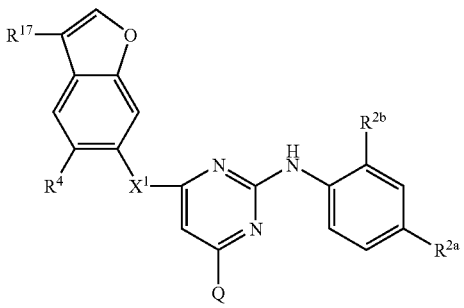

| No. | X¹ | Q | R⁴ | R¹⁷ | R²ᵃ | R²ᵇ |
|---|---|---|---|---|---|---|
| 5.4 | O | H | Cl | —CH₂—CN | —CO—NH₂ | H |
| 5.5 | O | H | Cl | —CH₂—CN | F | H |
| 5.6 | O | H | Cl | —CH₂—CN | Cl | H |
| 5.7 | O | H | Cl | —CH₂—CN | Br | H |
| 5.8 | O | H | Cl | —CH₂—CN | CN | OH |
| 5.9 | O | H | Cl | —CH₂—CN | CN | Cl |
| 5.10 | O | H | Cl | —CH₂—CN | F | F |
| 5.11 | O | H | Cl | —CH₂—CN | —CH₂—CO—NH₂ | H |
| 5.12 | O | CN | Cl | —CH₂—CN | CN | H |
| 5.13 | NH | CN | Cl | —CH₂—CN | CN | H |
| 5.14 | O | H | Cl | —CH₂—CO—NH₂ | CN | H |
| 5.15 | NH | H | Cl | —CH₂—CO—NH₂ | CN | H |

TABLE 7

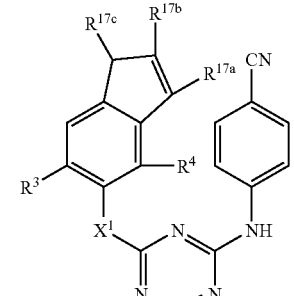

| N° | X¹ | R¹⁷ᵃ | R¹⁷ᵇ | R¹⁷ᶜ | R³ | R⁴ | Q |
|---|---|---|---|---|---|---|---|
| 7.1 | NH | —Cl | H | H | H | H | H |
| 7.2 | NH | —Br | H | H | H | H | H |
| 7.3 | NH | —CN | H | H | H | H | H |
| 7.4 | NH | —CH=CH—CN | H | H | H | H | H |
| 7.5 | NH | —CN | H | H | Cl | H | H |
| 7.6 | NH | —CN | H | H | CH₃ | CH₃ | H |
| 7.7 | O | —CN | H | H | CH₃ | CH₃ | H |
| 7.8 | O | —CN | H | H | Cl | H | H |
| 7.9 | NH | —CH₂—CN | H | H | Cl | H | H |
| 7.10 | O | —CH₂—CN | H | H | Cl | H | H |
| 7.11 | NH | —CH₂—CN | H | H | CH₃ | CH₃ | H |
| 7.12 | O | —CH₂—CN | H | H | CH₃ | CH₃ | H |

TABLE 6

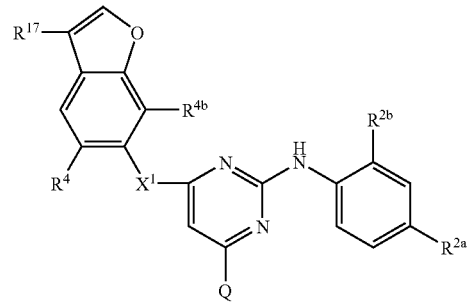

| No. | X¹ | Q | R⁴ᵃ | R⁴ᵇ | R¹⁷ | R²ᵃ | R²ᵇ |
|---|---|---|---|---|---|---|---|
| 6.1 | O | H | CH₃ | CH₃ | —CH₂—CN | —CH₂—CN | H |
| 6.2 | O | H | CH₃ | CH₃ | —CH₂—CN | —NO₂ | H |
| 6.3 | O | H | CH₃ | CH₃ | —CH₂—CN | 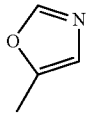 | H |
| 6.4 | O | H | CH₃ | CH₃ | —CH₂—CN | —CO—NH₂ | H |
| 6.5 | O | H | CH₃ | CH₃ | —CH₂—CN | F | H |
| 6.6 | O | H | CH₃ | CH₃ | —CH₂—CN | Cl | H |
| 6.7 | O | H | CH₃ | CH₃ | —CH₂—CN | Br | H |
| 6.8 | O | H | CH₃ | CH₃ | —CH₂—CN | CN | OH |
| 6.9 | O | H | CH₃ | CH₃ | —CH₂—CN | CN | Cl |
| 6.10 | O | H | CH₃ | CH₃ | —CH₂—CN | F | F |
| 6.11 | O | H | CH₃ | CH₃ | —CH₂—CN | —CH₂—CO—NH₂ | H |
| 6.12 | NH | CN | CH₃ | CH₃ | —CH₂—CN | CN | H |
| 6.13 | O | CN | CH₃ | CH₃ | —CH₂—CN | CN | H |
| 6.14 | O | H | CH₃ | CH₃ | —CH₂—CONH₂ | CN | H |
| 6.15 | NH | H | CH₃ | CH₃ | —CH₂—CONH₂ | CN | H |

TABLE 8

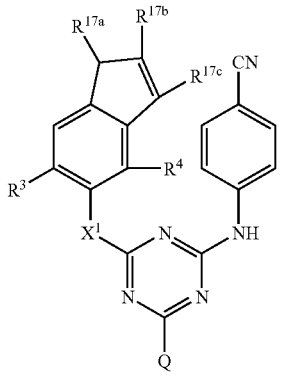

| N° | X¹ | R¹⁷ᵃ | R¹⁷ᵇ | R¹⁷ᶜ | R³ | R⁴ | Q |
|---|---|---|---|---|---|---|---|
| 8.1 | NH | —Cl | H | H | H | H | H |
| 8.2 | NH | —Br | H | H | H | H | H |
| 8.3 | NH | —CN | H | H | H | H | H |
| 8.4 | NH | —CH=CH—CN | H | H | H | H | H |
| 8.5 | NH | —CN | H | H | Cl | H | H |
| 8.6 | NH | —CN | H | H | CH₃ | CH₃ | H |
| 8.7 | O | —CN | H | H | CH₃ | CH₃ | H |
| 8.8 | O | —CN | H | H | Cl | H | H |

TABLE 9

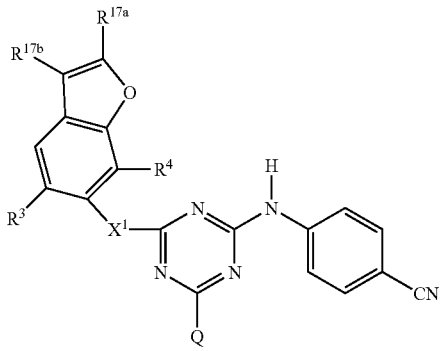

| N° | X¹ | R¹⁷ᵃ | R⁴ | R³ | Q | R¹⁷ᵇ |
|---|---|---|---|---|---|---|
| 9.1 | O | H | CH₃ | H | H | —CH₂CN |
| 9.2 | O | H | H | H | H | —CH₂CN |
| 9.3 | O | H | CH₃ | Cl | H | —CH₂CN |
| 9.4 | O | H | H | H | H | —CH(CH₃)—CN |
| 9.5 | O | H | CH₃ | H | H | —CH(CH₃)—CN |
| 9.6 | O | H | CH₃ | Cl | H | —CH(CH₃)—CN |
| 9.7 | O | H | H | H | H | —CN |
| 9.8 | O | H | CH₃ | H | H | —CN |
| 9.9 | O | H | CH₃ | Cl | H | —CN |
| 9.10 | NH | H | CH₃ | H | H | —CH₂CN |
| 9.11 | NH | H | H | H | H | —CH₂CN |
| 9.12 | NH | H | CH₃ | Cl | H | —CH₂CN |
| 9.13 | NH | H | H | H | H | —CH(CH₃)—CN |
| 9.14 | NH | H | CH₃ | H | H | —CH(CH₃)—CN |
| 9.15 | NH | H | CH₃ | Cl | H | —CH(CH₃)—CN |
| 9.16 | NH | H | H | H | H | —CN |
| 9.17 | NH | H | CH₃ | H | H | —CN |
| 9.18 | NH | H | CH₃ | Cl | H | —CN |
| 9.19 | O | CH₃ | CH₃ | H | H | —CH₂CN |
| 9.20 | O | CH₃ | H | H | H | —CH₂CN |
| 9.21 | N | CH₃ | CH₃ | H | H | —CH₂CN |
| 9.22 | N | CH₃ | H | H | H | —CH₂CN |
| 9.23 | O | H | H | H | H | CH₂-(2)Pyr |
| 9.24 | O | H | CH₃ | H | H | CH₂-(2)Pyr |
| 9.25 | O | H | CH₃ | Cl | H | CH₂-(2)Pyr |

TABLE 9-continued

| N° | X¹ | R¹⁷ᵃ | R⁴ | R³ | Q | R¹⁷ᵇ |
|---|---|---|---|---|---|---|
| 9.26 | O | H | H | H | H | CH₂-(3)Pyr |
| 9.27 | O | H | CH₃ | H | H | CH₂-(3)Pyr |
| 9.28 | O | H | CH₃ | Cl | H | CH₂-(3)Pyr |
| 9.29 | NH | H | H | H | H | CH₂-(2)Pyr |
| 9.30 | NH | H | CH₃ | H | H | CH₂-(2)Pyr |
| 9.31 | NH | H | CH₃ | Cl | H | CH₂-(2)Pyr |
| 9.32 | NH | H | H | H | H | CH₂-(3)Pyr |
| 9.33 | NH | H | CH₃ | H | H | CH₂-(3)Pyr |
| 9.34 | NH | H | CH₃ | Cl | H | CH₂-(3)Pyr |
| 9.35 | O | H | CH₃ | H | CH₃ | CH₂—CN |
| 9.36 | O | H | H | H | CH₃ | CH₂—CN |
| 9.37 | O | H | H | H | CH₃ | CH(CH₃)—CN |
| 9.38 | O | H | CH₃ | H | CH₃ | CH(CH₃)—CN |
| 9.39 | O | H | CH₃ | Cl | CH₃ | CH₂—CN |
| 9.40 | O | H | CH₃ | Cl | CH₃ | CH(CH₃)—CN |
| 9.41 | NH | H | CN₃ | H | CH₃ | CH₂—CN |
| 9.42 | NH | H | N | H | CH₃ | CH₂—CN |
| 9.43 | NH | H | H | H | CH₃ | CH(CH₃)—CN |
| 9.44 | NH | H | CH₃ | H | CH₃ | CH(CH₃)—CN |
| 9.45 | NH | H | CH₃ | Cl | CH₃ | CH₂—CN |
| 9.46 | NH | H | CH₃ | Cl | CH₃ | CH(CH₃)—CN |
| 9.47 | O | H | H | CH₃ | H | CH(CH₃)CN |
| 9.48 | O | H | CH₃ | CH₃ | H | CH(CH₃)CN |

TABLE 10

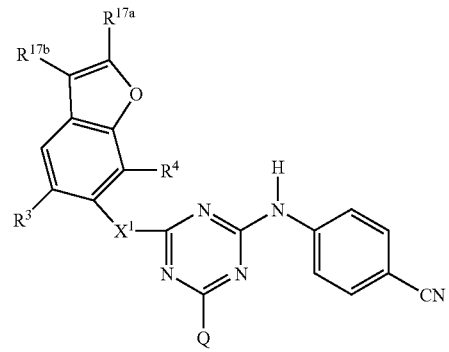

| No. | R¹⁷ | R⁴ | R³ |
|---|---|---|---|
| 10.1 | —H | —CH₃ | —H |
| 10.2 | —H | —H | —H |
| 10.3 | —H | —CH₃ | —Cl |
| 10.4 | —CH₃ | —CH₃ | —H |
| 10.5 | —CH₃ | —H | —H |
| 10.6 | H | —CH₃ | —H |
| 10.7 | —CH₃ | —CH₃ | —CH₃ |
| 10.8 | =CH—C₆H₅ | —CH₃ | H |
| 10.9 | =CH-(4-pyridinyl) | —CH₃ | H |
| 10.10 | =CH-(2-pyridinyl) | —CH₃ | H |
| 10.11 | =CH-(3-pyridinyl) | —CH₃ | H |

TABLE 11

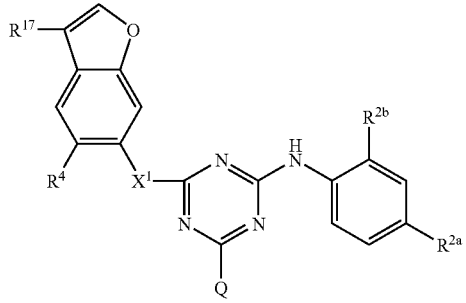

| No. | X¹ | Q | R⁴ | R¹⁷ | R²ᵃ | R²ᵇ |
|---|---|---|---|---|---|---|
| 11.1 | O | H | Cl | —CH₂—CN | —CH₂—CN— | H |
| 11.2 | O | H | Cl | —CH₂—CN | —NO₂ | H |
| 11.3 | O | H | Cl | —CH₂—CN | 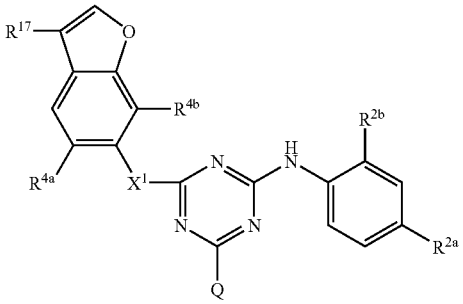 | H |
| 11.4 | O | H | Cl | —CH₂—CN | —CO—NH₂ | H |

TABLE 11-continued

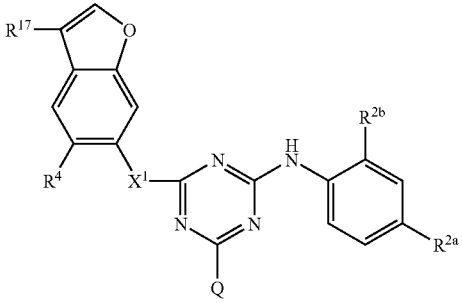

| No. | X¹ | Q | R⁴ | R¹⁷ | R²ᵃ | R²ᵇ |
|---|---|---|---|---|---|---|
| 11.5 | O | H | Cl | —CH₂—CN | F | H |
| 11.6 | O | H | Cl | —CH₂—CN | Cl | H |
| 11.7 | O | H | Cl | —CH₂—CN | Br | H |
| 11.8 | O | H | Cl | —CH₂—CN | CN | OH |
| 11.9 | O | H | Cl | —CH₂—CN | CN | Cl |
| 11.10 | O | H | Cl | —CH₂—CN | F | F |
| 11.11 | O | H | Cl | —CH₂—CN | —CH₂—CO—NH₂ | H |
| 11.12 | O | CN | Cl | —CH₂—CN | CN | H |
| 11.13 | NH | CN | Cl | —CH₂—CN | CN | H |

TABLE 12

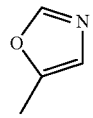

| No. | X¹ | Q | R⁴ᵃ | R⁴ᵇ | R¹⁷ | R²ᵃ | R²ᵇ |
|---|---|---|---|---|---|---|---|
| 13.1 | O | H | CH₃ | CH₃ | —CH₂—CN | —CH₂—CN | H |
| 13.2 | O | H | CH₃ | CH₃ | —CH₂—CN | —NO₂ | H |
| 13.3 | O | H | CH₃ | CH₃ | —CH₂—CN | (5-methyl-oxazolyl) | H |
| 13.4 | O | H | CH₃ | CH₃ | —CH₂—CN | —CO—NH₂ | H |
| 13.5 | O | H | CH₃ | CH₃ | —CH₂—CN | F | H |
| 13.6 | O | H | CH₃ | CH₃ | —CH₂—CN | Cl | H |
| 13.7 | O | H | CH₃ | CH₃ | —CH₂—CN | Br | H |
| 13.8 | O | H | CH₃ | CH₃ | —CH₂—CN | CN | OH |
| 13.9 | O | H | CH₃ | CH₃ | —CH₂—CN | CN | Cl |
| 13.10 | O | H | CH₃ | CH₃ | —CH₂—CN | F | F |
| 13.11 | O | H | CH₃ | CH₃ | —CH₂—CN | —CH₂—CO—NH | H |
| 13.12 | NH | CN | CH₃ | CH₃ | —CH₂—CN | CN | H |
| 13.13 | O | CN | CH₃ | CH₃ | —CH₂—CN | CN | H |

Formulation Examples

Capsules

Active ingredient, in casu a compound of formula (I), can be dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, can be dissolved in organic solvents such as ethanol, methanol methylene chloride. Suitably the polymer can be dissolved in ethanol. The polymer and compound solutions can be mixed and subsequently spray dried. The ratio of compound/polymer can be selected from 1/1 to 1/6. Intermediate ranges can be 1/1.5 and 1/3. A suitable ratio can be 1/6. The spray-dried powder, a solid dispersion, can subsequently be filled in capsules for administration. The drug load in one capsule can range between 50 and 100 mg depending on the capsule size used.

Film-Coated Tablets

Preparation of Tablet Core

A mixture of 100 g of active ingredient, in casu a compound of formula (I), 570 g lactose and 200 g starch can be mixed well and thereafter humidified with a solution of 5 g sodium dodecyl sulfate and 10 g polyvinylpyrrolidone in about 200 ml of water. The wet powder mixture can be sieved, dried and sieved again. Then there can be added 100 g microcrystalline cellulose and 15 g hydrogenated vegetable oil. The whole can be mixed well and compressed into tablets, giving 10.000 tablets, each comprising 10 mg of the active ingredient.

Coating

To a solution of 10 g methylcellulose in 75 ml of denaturated ethanol there can be added a solution of 5 g of ethylcellulose in 150 ml of dichloromethane. Then there can be added 75 ml of dichloromethane and 2.5 ml 1,2,3-propanetriol. 10 g of polyethylene glycol can be molten and dissolved in 75 ml of dichloromethane. The latter solution can be added to the former and then there can be added 2.5 g of magnesium octadecanoate, 5 g of polyvinylpyrrolidone and 30 ml of concentrated color suspension and the whole can be homogenated. The tablet cores can be coated with the thus obtained mixture in a coating apparatus.

Antiviral Analyses

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

Cellular Assay Experimental Method

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor. Wherever results are reported as e.g. $pEC_{50}$ or $pCC_{50}$ values, the result is expressed as the negative logarithm of the result expressed as $EC_{50}$ or $CC_{50}$ respectively.

Antiviral Spectrum

Because of the increasing emergence of drug resistant HIV strains, the present compounds were tested for their potency against clinically isolated HIV strains harboring several mutations. These mutations are associated with resistance to reverse transcriptase inhibitors and result in viruses that show various degrees of phenotypic cross-resistance to the currently commercially available drugs such as for instance AZT and delavirdine.

Table 13

The antiviral activity of the compound of the present invention has been evaluated in the presence of wild type HIV and HIV mutants bearing mutations at the reverse transcriptase gene. The activity of the compounds is evaluated using a cellular assay and the residual activity is expressed in $pEC_{50}$ values. Column A contains the $pEC_{50}$ against strain A (Strain A contains mutation 100I in HIV reverse transcriptase), Column B contains the $pEC_{50}$ against strain B (Strain B contains mutation 100I and 103N in HIV reverse transcriptase), Column C contains the $pEC_{50}$ against strain C (Strain C contains mutation 103N in HIV reverse transcriptase), Column D contains the pEC50 against strain D (Strain D contains mutation 181C in HIV reverse transcriptase), Column E contains the $pEC_{50}$ against strain E (Strain E contains mutation 188L in HIV reverse transcriptase), Column F contains the $pEC_{50}$ against strain F (Strain F contains mutation 227C in HIV reverse transcriptase), and Column G contains the $pEC_{50}$ against strain G (Strain G contains mutation 106A and 227L in HIV reverse transcriptase,). Column IIIB displays the $pEC_{50}$ value against wild type HIV-LAI strain. ND, not determined.

| Compound number | IIIB | A | B | C | D | E | F | G |
|---|---|---|---|---|---|---|---|---|
| 3.1 | 9.2 | 7.4 | ND | 8.5 | 8.2 | 7.4 | 7.6 | 8.3 |
| 3.61 | 7.5 | 5.5 | ND | 6.6 | 5.6 | 5.4 | 5.6 | 6.2 |

The invention claimed is:

1. A compound of formula (I)

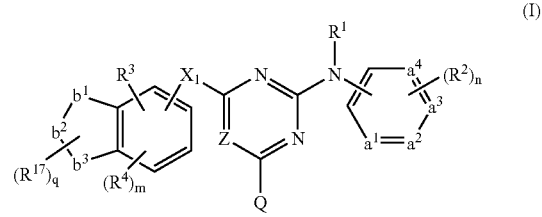

a pharmaceutically acceptable acid addition salt, or a stereochemically isomeric form thereof, wherein $-a^1=a^2-a^3=a^4-$ represents a bivalent radical of formula —CH=CH—CH=CH— (a-1);

$-b^1-b^2-b^3-$ represents a bivalent radical of formula

—O—CH$_2$—CH$_2$— (b-1);

—O—CH=CH— (b-2);

—CH$_2$—CH=CH— (b-5);

n is 1;
m is 0, 1;
q is 1,2;
$R^1$ is hydrogen;
$R^2$ is halo, nitro, cyano, —CONH$_2$, C$_{1-6}$alkyl optionally substituted with cyano or with —CONH$_2$;
$X_1$ is —NH—, —O—;
$R^3$ is hydrogen, halo, C$_{1-6}$alkyl;
$R^4$ is halo, C$_{1-6}$alkyl;
$R^{13}$ and $R^{14}$ each independently are hydrogen, C$_{1-6}$alkyl;
$R^{17}$ is cyano, halo, C$_{1-6}$alkyl optionally substituted with cyano; C$_{2-6}$alkenyl optionally substituted with cyano; and, where possible, $R^{17}$ may also be attached to the $-b^1-b^2-b^3-$moiety by a double bond whereby $R^{17}$ is =O; the $R^{17}$ moiety attached to a carbon atom in the $-b^1-b^2-b^3$ ring;
Q represents hydrogen;
Z is C—Y, wherein Y is hydrogen or halo.

2. The compound of claim 1 wherein:
n is 1;
q is 1.

3. The compound of claim 1 wherein $R^2$ is cyano.

4. The compound of claim 1 wherein Y is hydrogen.

5. The compound of claim 1 wherein $R^{17}$ is cyano, C$_{1-6}$alkyl substituted with cyano, C$_{2-6}$alkenyl substituted with cyano; or $R^{17}$ is =O.

6. The compound of claim 1 wherein $-b^1-b^2-b^3-$ represents a bivalent radical of formula —O—CH$_2$—CH$_2$— (b-1);

n is 1;
m is 0;
q is 1;
$R^2$ is cyano;
Y is hydrogen;
$R^{17}$ is =O.

7. The compound of claim 1 wherein $-b^1-b^2-b^3-$ represents a bivalent radical of formula —O—CH=CH— (b-2);

n is 1;
m is 0;
q is 1;
$R^2$ is cyano;
Y is hydrogen;
$R^{17}$ is C$_{1-6}$alkyl substituted with cyano.

8. The compound of claim 1 wherein $-b^1-b^2-b^3-$ represents a bivalent radical of formula, —CH$_2$—CH=CH— (b-5);

n is 1;
m is 0;
q is 1;
$R^2$ is cyano;
$R^3$ is halo;
Y is hydrogen;
$R^{17}$ is C$_{1-6}$alkyl substituted with cyano.

9. A pharmaceutical composition comprising an effective amount, against HIV infection, of a compound of claim 1, in a pharmaceutically acceptable carrier.

10. A pharmaceutical composition of claim 9 and another antiretroviral compound.

11. A method of treating HIV infection by administering to a human subject in need of such treatment, an anti-HIV effective amount of a compound of claim 1.

* * * * *